(12) United States Patent
Miyake et al.

(10) Patent No.: US 7,919,305 B2
(45) Date of Patent: Apr. 5, 2011

(54) METHOD FOR MANUFACTURING CELL CULTURE SUBSTRATE

(75) Inventors: Hideyuki Miyake, Tokyo (JP); Hideshi Hattori, Tokyo (JP); Yoichi Takahashi, Tokyo (JP)

(73) Assignee: Dai Nippon Printing Co., Ltd., Tokyo-to (JP)

( * ) Notice: Subject to any disclaimer, the term of this patent is extended or adjusted under 35 U.S.C. 154(b) by 0 days.

(21) Appl. No.: 11/062,674

(22) Filed: Feb. 22, 2005

(65) Prior Publication Data

US 2005/0279730 A1  Dec. 22, 2005

(30) Foreign Application Priority Data

Feb. 19, 2004  (JP) .................. 2004-042443

(51) Int. Cl.
*C12M 1/34* (2006.01)
*C12M 1/36* (2006.01)
*C12M 1/38* (2006.01)
*C12M 3/00* (2006.01)
*C12M 1/00* (2006.01)
*C12N 5/00* (2006.01)
*C12N 5/02* (2006.01)

(52) U.S. Cl. ............. 435/286.2; 435/289.1; 435/402

(58) Field of Classification Search .......... 435/287.1, 435/289.1, 402, 286.7, 286.2, 286.4
See application file for complete search history.

(56) References Cited

U.S. PATENT DOCUMENTS

| | | | |
|---|---|---|---|
| 4,789,601 A | 12/1988 | Banes | |
| 5,096,941 A | 3/1992 | Harnden | |
| 5,202,227 A | 4/1993 | Matsuda et al. | |
| 5,284,766 A | 2/1994 | Okano et al. | |
| 5,470,739 A | 11/1995 | Akaike et al. | |
| 5,512,131 A | 4/1996 | Kumar et al. | |
| 5,602,029 A | 2/1997 | Miyamoto | |
| 5,669,303 A | 9/1997 | Maracas et al. | |
| 5,721,131 A | 2/1998 | Rudolph et al. | |
| 5,725,788 A | 3/1998 | Maracas et al. | |
| 5,900,160 A | 5/1999 | Whitesides et al. | |
| 5,981,425 A | 11/1999 | Taoda et al. | |
| 6,294,313 B1 | 9/2001 | Kobayashi et al. | |
| 6,368,838 B1 | 4/2002 | Singhvi et al. | |
| 2002/0095219 A1 | 7/2002 | Nelles et al. | |
| 2002/0182633 A1* | 12/2002 | Chen et al. ................ 435/7.1 |
| 2003/0089259 A1 | 5/2003 | Damme et al. | |
| 2003/0219889 A1* | 11/2003 | Sumaru et al. .......... 435/287.1 |
| 2004/0235167 A1 | 11/2004 | Miyake et al. | |
| 2005/0186674 A1 | 8/2005 | Miyake et al. | |
| 2005/0208656 A1 | 9/2005 | Miyake et al. | |
| 2005/0255594 A1 | 11/2005 | Miyake et al. | |
| 2005/0266319 A1 | 12/2005 | Miyake et al. | |
| 2005/0279730 A1 | 12/2005 | Miyake et al. | |
| 2006/0019390 A1 | 1/2006 | Miyake et al. | |
| 2006/0183219 A1 | 8/2006 | Miyake et al. | |

FOREIGN PATENT DOCUMENTS

| | | |
|---|---|---|
| EP | 1 246 011 A2 | 10/2002 |
| JP | 2-211865 | 8/1990 |
| JP | 2-245181 | 9/1990 |
| JP | 3-7576 | 1/1991 |
| JP | 03-198771 | 8/1991 |
| JP | 04-4869 | 1/1992 |
| JP | 04-94679 | 3/1992 |
| JP | 04-126071 | 4/1992 |
| JP | 04-126074 | 4/1992 |
| JP | 5-176753 | 7/1993 |
| JP | 6-335381 | 12/1994 |
| JP | 07-075547 | 3/1995 |
| JP | 07-099962 | 4/1995 |
| JP | 07-308186 | 11/1995 |
| JP | 08-009960 | 1/1996 |
| JP | 9-240125 | 9/1997 |
| JP | 10-12545 | 1/1998 |
| JP | 2002-184752 | 6/2002 |
| JP | 2002-253204 | 9/2002 |
| JP | 2002-274077 | 9/2002 |
| JP | 2002-355026 | 12/2002 |
| JP | 2002-355031 | 12/2002 |
| JP | 2002-542883 | 12/2002 |
| JP | 2003-9860 | 1/2003 |
| JP | 2003-38170 | 2/2003 |

(Continued)

OTHER PUBLICATIONS

G. Sagvolden et al. "Cell adhesion force microscopy" Proc. Natl. Acad. Sci. USA vol. 96, pp. 471-476, Jan. 1999.*

(Continued)

*Primary Examiner* — Sandra E. Saucier
*Assistant Examiner* — Thane Underdahl
(74) *Attorney, Agent, or Firm* — Ladas & Parry LLP

(57) ABSTRACT

A main object of the invention is to provide a new method for producing a cell culture substrate used to cause cells to adhere in a highly precise form onto a base material and then culture the cells.

To attain the object, the invention provides a method for producing a cell culture substrate comprising: a patterning substrate forming process of forming, on a base material, a cell culture patterning layer wherein a cell adhesion portion having cell adhesive properties and a cell adhesion-inhibiting portion having cell adhesion-inhibiting properties can be formed by action of a photocatalyst by energy irradiation, thereby forming a patterning substrate; an energy irradiating process of irradiating the energy onto the cell culture patterning layer, thereby forming the cell adhesion portion and the cell adhesion-inhibiting portion in a pattern form by action of the photocatalyst; and a cell-containing liquid applying process of applying a cell-containing liquid onto the cell adhesion portion by a region-selecting applying method of applying the cell-containing liquid selectively onto the patterned cell adhesion portion.

3 Claims, 4 Drawing Sheets

FOREIGN PATENT DOCUMENTS

| | | | |
|---|---|---|---|
| JP | 2003-039399 | | 2/2003 |
| JP | 2003339373 | * | 2/2003 |
| JP | 2003-228172 | | 8/2003 |
| JP | 2003-295428 | | 10/2003 |
| JP | 2003-339373 | | 12/2003 |
| JP | 2004-51 | | 1/2004 |
| JP | 2004-57019 | | 2/2004 |
| JP | 2004-344025 | | 12/2004 |
| WO | 98/51785 | | 11/1998 |

OTHER PUBLICATIONS

Chemindustry.com "tetramethoxysilane" 1999-2008 chemindustry.com Inc 2pgs.*

Wilson, Jr., W. Cris, and Thomas Boland. "Cell and Organ Printing 1: Protein and Cell Printers." *The Anatomical Record Part A* 272A (2003): 491-496.

G. Sagvolden, et al; "Cell adhesion force microscopy", Proc. Natl. Acad. Sci. USA, vol. 96, pp. 471-476, Jan. 1999 Biophysics.

B.J. Spargo, etl al; "Spatially controlled adhesion, spreading, and differentiation of endothelial cells on self-assembled molecular monolayers" Proc. Natl. Acad. Sci. USA, vol. 91, pp. 11070-11074, Nov. 1994, Cell Biology.

Dan V. Nicolau, et al; "Control of the neuronal cell attachment by functionality manipulation of diazo-naphtho-quinone/novolak photoresist surface", Biosensors & Bioelectronics vol. 11. No. 12, pp. 1237-1252, 1996.

Woon-Seok Yeo, et al; "Electroactive Monolayer Substrates that Selectively Release Adherent Cells", Chembiochem 2001, No. 7/8, pp. 590-593.

Kyung-Soon Cho, et al; "The Effect of Energy Irradiation on the Volum Resistivity Properties of Low Density Polyethylene Film", Conference Record of the 1998 IEEE International Symposium on Electrical Insulation, Arlington, Virginia, USA, Jun. 7-10, 1998, pp. 194-196.

W. Chris Wilson, Jr. et al; "Cell and Organ Printing 1: Protein and Cell Printers", The Anatomical Record, Part A 272A: 491-496(2003).

Seiya Takahashi, et al; "A Study of Handling of Living Mammalian Cells Using a Piezoelectric Dispensing Head", Japanese Journal of Applied Physics, Part I, 2003, vol. 42, No. 5B, pp. 3098-3101.

M Nakamura, et al; "Cell Jet Printing by Inkjet Technology", Proceeding for 25th Convention for Japan Soc. For Biomaterials, Tokyo Medical and Dental University Institute of Biomaterials and Bioengineering, Seiko Epson Corp, 2003, p. 221.

M. Nakamura, et al; "Study on a cell micro-disseminating method using an inkjet" <Jinkoh Zoki (translation: artificial internal organ), 2003, vol. 32, No. 2, p. S-67>, Tokyo Medical and Dental University Institute of Biomaterials and Bioengineering, Seiko Epson Corp, et al.

* cited by examiner

METHOD FOR MANUFACTURING CELL CULTURE SUBSTRATE

BACKGROUND OF THE INVENTION

1. Field of the Invention

The present invention relates to a method for producing a cell culture substrate on which cells are caused to adhere in a highly precise pattern form.

2. Description of the Related Art

At present, cell cultures of various animals and plants are performed, and also new cell culture methods are in development. The technologies of the cell culture are utilized, such as, to elucidate the biochemical phenomena and natures of cells and to produce useful substances. Furthermore, with cultured cells, an attempt to investigate the physiological activity and toxicity of artificially synthesized medicals is under way.

Some cells, particularly a lot of animal cells have the adhesion dependency of adhering to some materials and growing thereon, and cannot survive for a long period under a flotation condition out of organisms. For culturing cells having such adhesion dependency, a carrier to which cells can adhere is necessary, and in general, a plastic culturing plate with uniformly applied cell adhesive proteins such as collagen, fibronectin and the like is used. It is known that these cell adhesive proteins act on cultured cells, make the cells adhere easily, and exert an influence on the form of cells.

On the other hand, there is a technology reported of adhering cultured cells only onto a small part on a base material and arranging them. By such a technology, it is made possible to apply cultured cells to artificial organs, biosensors, bioreactors and the like. As the method of arranging cultured cells, there is a method adopted in which a base material having a surface that forms a pattern different in easiness of adhesion to cells is used, cells are cultured on the surface of this base material and allowed to adhere only onto surfaces processed so that cells adhere, and thereby the cells are arranged.

For example, in Japanese Patent Application Laid-Open (JP-A) No. 2-245181, an electric charge-retaining medium on which an electrostatic pattern is formed is applied to culture cells for the purpose of proliferating nerve cells in a form of circuit, and the like. Furthermore, JP-A No. 3-7576 tries to arrange cultured cells on a surface on which a cell adhesion-inhibiting or cell adhesive photosensitive hydrophilic polymer has been patterned by a photolithography method.

Furthermore, JP-A No. 5-176753 discloses a cell culture base material on which a substance such as collagen and the like affecting on the adhesion ratio and form of cells is patterned, and a method of producing this base material by a photolithography method. By culturing cells on such a base material, a larger amount of cells can be adhered on a surface on which collagen or the like is patterned, to realize patterning of cells.

However, such patterning of cell culture regions may be required to be highly precise depending on applications. In the case of conducting patterning by a photolithography method using a photosensitive material as described above, a highly precise pattern can be obtained; however, a cell adhesive material is required to have photosensitivity, and it is difficult in many cases to conduct chemical modification to impart such photosensitivity to, for instance, biopolymers and the like; thereby leading to extremely narrow width in selectivity of cell adhesive materials, problematically. Furthermore, in a photolithography method using a photo resist, it is necessary to use a liquid developer and the like, and these can affect adversely in culturing cells in some cases.

Furthermore, as a method of forming a highly precise pattern of a cell adhesive material, a Micro Contact Printing method is proposed by George M. Whitesides, Harvard University (for example, U.S. Pat. Nos. 5,512,131 and 5,900,160, JP-A Nos. 9-240125 and 10-12545 etc). However, there is a problem in that it is difficult to industrially produce a cell culture base material having a pattern of a cell adhesive material using this method.

SUMMARY OF THE INVENTION

Thus, it has been desired to provide a new method for producing a cell culture substrate used to cause cells to adhere in a highly precise pattern onto a base material and then culture the cells.

The present invention provides a method for producing a cell culture substrate, comprising: a patterning substrate forming process of forming, on a base material, a cell culture patterning layer wherein a cell adhesion portion having cell adhesive properties and a cell adhesion-inhibiting portion having cell adhesion-inhibiting properties can be formed by an action of a photocatalyst by energy irradiation, thereby forming a patterning substrate; an energy irradiating process of irradiating an energy onto the cell culture patterning layer, thereby forming the cell adhesion portion and the cell adhesion-inhibiting portion in a pattern form by the action of the photocatalyst; and a cell-containing liquid applying process of applying a cell-containing liquid onto the cell adhesion portion by a region-selecting applying method of applying the cell-containing liquid selectively onto the cell adhesion portion in the patterned form.

In the present invention, a cell-containing liquid is applied on to the cell adhesion portion, which is formed in a pattern form by action of a photocatalyst, by a region-selecting applying method of applying the cell-containing liquid selectively, such as ink-jetting method; therefore, it is possible to produce a cell culture substrate wherein the adhesion pattern of cells is highly precise. For example, in the case of forming cellar tissues or the like, it is necessary to cause two or more kinds of cells to adhere onto a single substrate; according to the present invention, two or more kinds of cells can be extremely easily caused to adhere onto a single substrate.

The conventionally-performed method of inoculating cells onto the whole surface of a base material and then patterning the cells is ordinarily a method of inoculating more cells than cells to be actually patterned onto the whole and then washing off the cells which are left over without being patterned. Therefore, loss is generated out of the used cells. For this reason, it is difficult to apply such a patterning method to the case of the kind of cells which cannot be easily obtained. On the other hand, the present invention has the following advantages that: a loss of the number of cells can be decreased since the cell-containing liquid is applied only onto a target region; and thus various kinds of cells can be patterned.

The method of the invention for producing a cell culture substrate can be classified into 6 embodiments, dependently on difference in the kind of the patterning substrate in the patterning substrate forming process and in the energy irradiating process.

The method of the first embodiment for producing a cell culture substrate is a method wherein: the above-mentioned patterning substrate comprises a base material, and a cell culture patterning layer which is formed on the base material and has a photocatalyst-containing cell adhesive layer comprising at least a photocatalyst and a cell adhesive material which has cell adhesive properties and is decomposed or denatured by action of the photocatalyst on the basis of energy irradiation; and the energy irradiating process is a process of irradiating the energy from a given direction, thereby forming a pattern composed of a cell adhesion-inhibiting portion where the cell adhesive material comprised in the photocatalyst-containing cell adhesive layer is decomposed or denatured, and a cell adhesion portion which is other than the cell adhesion-inhibiting portion.

The method of the second embodiment for producing a cell culture substrate is a method wherein: the above-mentioned patterning substrate comprises a base material, and a cell culture patterning layer which is formed on the base material and has a photocatalyst-containing cell adhesion-inhibiting material layer comprising at least a photocatalyst and a cell adhesion-inhibiting material which has cell adhesion-inhibiting properties of inhibiting adhesion onto cells and is decomposed or denatured by action of the photocatalyst on the basis of energy irradiation; and the energy irradiating process is a process of irradiating the energy from a given direction, thereby forming a pattern composed of a cell adhesion portion where the cell adhesion-inhibiting material comprised in the photocatalyst-containing cell adhesion-inhibiting material layer is decomposed or denatured, and a cell adhesion-inhibiting portion which is other than the cell adhesion portion.

In the first and second embodiments, their cell culture patterning layers have the photocatalyst-containing cell adhesive layer and the photocatalyst-containing cell adhesion-inhibiting material layer, respectively, which each comprise the photocatalyst; therefore, the cell culture patterning layer can be rendered a single layer. Thus, the embodiments are advantageous from the viewpoint of process, and give a good patterning sensitivity.

The method of the third embodiment for producing a cell culture substrate is a method wherein: the patterning substrate comprises a base material, and a cell culture patterning layer which is formed on the base material and has a photocatalyst-containing layer comprising at least a photocatalyst and a cell adhesive layer formed on the photocatalyst-containing layer; the cell adhesive layer at least comprises a cell adhesive material which has cell adhesive properties and is decomposed or denatured by action of the photocatalyst on the basis of energy irradiation; and the energy irradiating process is a process of irradiating the energy from a given direction, thereby forming a pattern composed of a cell adhesion-inhibiting portion where the cell adhesive material comprised in the cell adhesive layer is decomposed or denatured, and a cell adhesion portion which is other than the cell adhesion-inhibiting portion.

The method of the fourth embodiment for producing a cell culture substrate is a method wherein: the above-mentioned patterning substrate comprises a base material, and a cell culture patterning layer which is formed on the base material and has a photocatalyst-containing layer comprising at least a photocatalyst and a cell adhesion-inhibiting material layer formed on the photocatalyst-containing layer; cell adhesion-inhibiting material layer comprises a cell adhesion-inhibiting material which has cell adhesion-inhibiting properties of inhibiting adhesion onto the cells and is decomposed or denatured by action of the photocatalyst on the basis of energy irradiation; and the energy irradiating process is a process of irradiating the energy from a given direction, thereby forming a pattern composed of a cell adhesion portion where the cell adhesion-inhibiting material comprised in the cell adhesion-inhibiting material layer is decomposed or denatured and a cell adhesion-inhibiting portion which is other than the cell adhesion portion.

In the third and fourth embodiments, the cell adhesive layer and the cell adhesion-inhibiting material layer are formed on the photocatalyst-containing layer; accordingly, the possibility that cells directly contact the photocatalyst is small. For this reason, the embodiments have an advantage that a fear that cells deteriorates with the passage of time is decreased. Furthermore, these embodiments also have an advantage that the embodiments can be carried out even if the photocatalyst material cannot be mixed directly with the cell adhesive material or cell adhesion-inhibiting material.

The method of the fifth embodiment for producing a cell culture substrate is a method wherein: the above-mentioned patterning substrate comprises a base material and a cell culture patterning layer which is formed on the base material and has a cell adhesive layer comprising a cell adhesive material that has cell adhesive properties and is decomposed or denatured by action of a photocatalyst on the basis of energy irradiation; and the energy irradiating process is a process of arranging the cell adhesive layer and a photocatalyst-containing layer side substrate having a base body and a photocatalyst-containing layer comprising the photocatalyst to dispose the cell adhesive layer and the photocatalyst-containing layer facing each other, and then irradiating the energy onto the resultant from a given direction, thereby forming a pattern composed of a cell adhesion-inhibiting portion where the cell adhesive material comprised in the cell adhesive layer is decomposed or denatured, and a cell adhesion portion which is other than the cell adhesion-inhibiting portion.

The method of the sixth embodiment for producing a cell culture substrate is a method wherein: the above-mentioned patterning substrate comprises a base material and a cell culture patterning layer which is formed on the base material and has a cell adhesion-inhibiting material layer comprising a cell adhesion-inhibiting material that has cell adhesion-inhibiting properties of inhibiting adhesion onto cells and is denatured by action of a photocatalyst on the basis of energy irradiation; and the energy irradiating process is a process of arranging the cell adhesion-inhibiting material layer and a photocatalyst-containing layer side substrate having a base body and a photocatalyst-containing layer comprising the photocatalyst to dispose the cell adhesion-inhibiting material layer and the photocatalyst-containing layer facing each other, and then irradiating the energy onto the resultant from a given direction, thereby forming a pattern composed of a cell adhesion portion where the cell adhesion-inhibiting material comprised in the cell adhesion-inhibiting material layer is decomposed or denatured, and a cell adhesion-inhibiting portion which is other than the cell adhesion portion.

The fifth and sixth embodiments have an advantage that the cell culture substrate itself does not need to contain any photocatalyst and thus the possibility that cells deteriorate with the passage of time is small.

In the methods of the second, fourth and sixth embodiments for producing a cell culture substrate of the present invention, it is preferred that the cell adhesion portion is a hydrophilic region and the cell adhesion-inhibiting portion is a water-repellent region for the following reasons. In the case of applying a cell-containing liquid by use of the region-selecting applying method of applying the cell-containing liquid selectively, such as ink-jetting method, the cell-containing liquid can be highly precisely applied onto the cell adhesion portion on the basis of the matter that the cell adhesion portion is hydrophilic and the cell adhesion-inhibiting portion is water repellent since the cell-containing liquid is a hydrophilic material or an aqueous solution. Also, when cells are caused to adhere onto the boundary region between hydrophilic and water repellent regions, which have different natures, a change in the form of the cells, such as extension or orientation, may be caused in accordance with the kind of the cells. According to a report, such a change promotes the organization of the cells. According to the above-mentioned methods, such a change in the form of cells can be promoted as the case may be (see, for example, Donald E. Ingber et al., Journal of Cell Biology (1989), pp. 317-, and Kevin E. Healy, et al., Biotechnology and Bioengineering (1994), pp. 792-).

In the method of the invention for producing a cell culture substrate, light-shielding portions may be formed on the base material or the photocatalyst-containing layer in a pattern form. When the light-shielding portions are formed in this way, troublesome steps, such as a positioning step, are unnecessary since it is unnecessary to use any photomask at the time of energy irradiation. Moreover, a more highly precise pattern can be obtained in this case than in the case of using a photomask or the like since the distance between the cell culture patterning layer and the light-shielding portions are extremely small.

Furthermore, in the production method of the invention, it is preferred that the region-selecting applying method is ink-jetting method. According to this, the production can be made effective.

The present invention also provides an ink-jetting cell-containing liquid comprising cells, a culture solution and a biological cell adhesive material, and jets out in a pattern form onto a substrate by ink-jetting method, thereby forming a cell culture substrate onto which the cells adhere in the pattern form. This ink-jetting cell-containing liquid is good in adhesive property to the substrate. In general, biological cell adhesive materials are high in viscosity. By incorporating such a biological cell adhesive material into the cell-containing liquid, the viscosity of the cell-containing liquid can be raised to prevent the cells jetted out from moving around in the cell-containing liquid.

The present invention also provides an ink-jetting cell-containing liquid jets out in a pattern form onto a substrate by ink-jetting method to form a cell culture substrate onto which cells adhere in the pattern form, and the cells being micro-encapsulated. Since the cells are micro-encapsulated, the cells are not damaged, for example, when the cell-containing liquid is jetted out. As a result, a good-quality cell culture substrate can be produced.

These ink-jetting cell-containing liquids are preferably used when the region-selecting applying method is ink-jetting method in the method of the invention for producing a cell patterning substrate. The ink-jetting method referred to herein is a method of jetting out cells or a cell liquid. The system for the ink-jetting may be selected at will if the system does not give any damage to cells. Examples thereof include piezoelectrically driving, bubble jetting (registered trade mark), electrostatic jetting, electric field jetting, ultrasonic jetting, centrifugal jetting, and inertial force head systems. The piezoelectrically driving system is particularly preferred since the system does not give any damage to cells.

The present invention also provides an ink-jetting device for producing a cell culture substrate comprising a cell-containing liquid supplying section into which a cell-containing liquid is filled, a jetting-out section having a piezoelectrically driving head unit for jetting out the cell-containing liquid supplied from the cell-containing liquid supplying section onto a cell culture patterning substrate, and a stage for fixing the cell culture patterning substrate, wherein the cell-containing liquid supplying section is provided with a stirring means for dispersing cells homogeneously in the cell-containing liquid filled, and the jetting-out section and the stage are provided with one or more temperature controlling means for keeping the temperature of the cell-containing liquid constant before and after the jetting-out. By use of this ink-jetting device for producing a cell culture substrate, a high-quality cell culture substrate can be produced.

This device is preferably provided with a humidity controlling means for controlling the humidity between the piezo-electrically driving head unit and the cell culture patterning substrate fixed onto the stage. The device makes it possible to prevent the extinction or damage of cells based on the drying of the cell-containing liquid, a drop in activity of the cells, and the like.

DESCRIPTION OF THE PREFERRED EMBODIMENTS

Figure 1A:
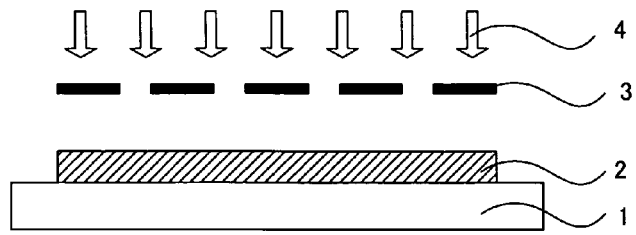
FIGS. 1A and 1B are process charts illustrating an example of the energy irradiating process in the method of the invention for producing a cell culture substrate.

The present invention relates to a cell culture substrate producing method which can give a cell culture substrate onto which cells adhere in a highly precise pattern form; an ink-jetting cell-containing liquid (i.e., a cell-containing liquid for ink-jet) which is preferably used to produce a cell culture substrate by ink-jetting method; and an ink-jetting device for producing effectively a cell culture substrate having a high quality. The following will describe them separately.

A. Method for Producing a Cell Culture Substrate

First, the method of the invention for producing a cell culture substrate is described. The method is a method for producing a cell culture substrate, comprising: a patterning substrate forming process of forming, on a base material, a cell culture patterning layer wherein a cell adhesion portion having cell adhesive properties and a cell adhesion-inhibiting portion having cell adhesion-inhibiting properties can be formed by action of a photocatalyst by energy irradiation, thereby forming a patterning substrate; an energy irradiating process of irradiating the energy onto the cell culture patterning layer, thereby forming the cell adhesion portion and the cell adhesion-inhibiting portion in a pattern form by action of the photocatalyst; and a cell-containing liquid applying process of applying a cell-containing liquid onto the cell adhesion portion by a region-selecting applying method of applying the cell-containing liquid selectively onto the patterned cell adhesion portion.

In the method of the invention for producing a cell culture substrate, a cell-containing liquid is applied onto the cell adhesion portion by the region-selecting applying method capable of applying the liquid selectively; therefore, a cell culture substrate having a highly precise pattern can be produced. Since such an applying method is used, plural kinds of cell-containing liquids can be applied. Accordingly, the present method can be effectively used to form, for example, cellar tissues composed of plural kinds of cells.

When cells are caused to adhere onto a cell culture region and cultured to form tissues, it is generally necessary that individuals of the cells are subjected to form-change, and arranged. In the case of applying a cell-containing liquid onto an ordinary base material, it is difficult to cause this form-change or arrangement and thus form tissues. On the other hand, according to the invention, a cell-containing liquid is applied onto the cell adhesion portion of the cell culture patterning layer, which has the cell adhesion portion and the cell adhesion-inhibiting portion. It is possible that the cells applied onto the cell adhesion portion are easily arranged or subjected to form-change along the pattern composed of the cell adhesion portion and the cell adhesion-inhibiting portion. Thus, the present method has an advantage that tissues are easily formed.

The following will describe each of the processes in the method of the invention for producing a cell culture substrate.

1. Patterning Substrate Forming Process

The patterning substrate forming process in the invention is a process of forming, on a base material, a cell culture patterning layer wherein a cell adhesion portion having cell adhesive properties and a cell adhesion-inhibiting portion having cell adhesion-inhibiting properties can be formed by action of a photocatalyst by energy irradiation, thereby forming a patterning substrate.

In the present process, the method for forming a cell culture patterning layer on a base material to form a patterning substrate may be selected from various methods in accordance with the kind of the cell culture patterning layer. The method may be, for example, a wet process such as spin coating, spray coating, dip coating, roll coating, bead coating or die coating, or a dry process such as PVD or CVD. The adsorption process also can be preferably used.

This patterning substrate forming process can be classified into 6 embodiments in accordance with the kind of the patterning substrate to be formed.

(1) First Embodiment

First, the patterning substrate formed according to the first embodiment of the present process is a patterning substrate comprising a base material, and a cell culture patterning layer which is formed on the base material and has a photocatalyst-containing cell adhesive layer comprising at least a photocatalyst and a cell adhesive material which has cell adhesive properties and is decomposed or denatured by action of the photocatalyst on the basis of energy irradiation.

The photocatalyst-containing cell adhesive layer contained in the cell culture patterning layer formed in the present embodiment comprises therein the photocatalyst; therefore, in the energy irradiating process which will be detailed later, at the time of irradiating energy, the cell adhesive material in the layer can be decomposed or denatured by action of the photocatalyst. It is therefore unnecessary to form a layer comprising any photocatalyst separately, or the like in the cell culture patterning layer. Thus, the cell culture patterning layer can be rendered a single layer. This is preferred from the viewpoint of production efficiency and the like. If necessary, the cell culture patterning layer may be formed to comprise a layer other than the photocatalyst-containing cell adhesive layer.

The following will describe the base material used in the patterning substrate forming process of the present embodiment, and the photocatalyst-containing cell adhesive layer formed in the present embodiment.

(Base Material)

First, the base material used in the embodiment is described. The base material is not limited to any special kind if the cell culture patterning layer having the photocatalyst-containing cell adhesive layer that will be detailed later can be formed on this base material. For example, the following can be used: an inorganic material such as metal, glass, silicon; or an organic material such as plastic.

The flexibility and the like of the base material is appropriately selected in accordance with the kind or use purpose of the cell culture substrate to be finally obtained. The transparency of the base material is appropriately selected in accordance with the kind of the cell culture substrate, the irradiation direction of energy irradiated to decompose or denature the cell adhesive material in the energy irradiating process, which will be detailed later, or other factors. When the energy is irradiated from the side of the base material, or the like, the base material needs to be transparent.

Figure 7A:
FIGS. 7A and 7B are each a schematic sectional view for explaining a base material used in the method of the invention for producing a cell culture substrate.
Figure 7B:

In the present embodiment, the base material may be a flat base material or a base material wherein one or more concave portions are formed. The base material may be a base material wherein a single concave portion is formed as shown in FIG. 7A, or a base material wherein plural concave portions are formed as shown in FIG. 7B.

At this time, side walls of the base material having the concave portion(s) may be treated in such a manner that the photocatalyst-containing cell adhesive layer which will be detailed later will not be formed thereon. Examples of the method for such a treatment include a method of using a mask or the like to cause a material having liquid repellency to adhere only onto the side walls by CVD; and a method of causing a material having liquid repellency to adhere onto the entire surface of the concave portion(s) and then using a cylindrical mask or the like to conduct ultraviolet ray treatment, plasma treatment or some other treatment, thereby making only the bottom face(s) of the concave portion(s) lyophilic.

In the present embodiment, the base material may be washed with a medical liquid, such as an alkali solution, and may be subjected to dry washing, such as oxygen plasma treatment or ultraviolet treatment. In this case, the wettability of a coating solution for forming the photocatalyst-containing cell adhesive layer is improved. Furthermore, this case has an advantage that the adhesive property of the base material to the photocatalyst-containing cell adhesive layer is improved since reactive functional groups are arranged on the surface of the base material.

On the base material according to the present embodiment, as needed, a light-shielding portion may be formed. The light-shielding portion that can be used in the embodiment, as far as it can shield energy that is irradiated on the patterning substrate, is not particularly restricted. For instance, a metal thin film that is made of chromium or the like and formed into a thickness of about 1000 to 2000 Å by a sputtering method, a vacuum deposition method or the like is formed and patterned to form a shielding portion. As the patterning method, an ordinary patterning method such as the sputtering can be used.

A method may be one by which a layer that contains light-shielding particles such as carbon particulates, metal oxides, inorganic pigments and organic pigments in a resin binder is formed in a pattern. As the resin binders that can be used, a polyimide resin, acrylic resin, epoxy resin, polyacrylamide, polyvinyl alcohol, gelatin, casein, cellulose and the like can be used singularly or in combination of two or more kinds, and furthermore a photosensitive resin and an O/W emulsion type resin composition such as emulsified reactive silicone can be used. A thickness of such resinous light-shielding portion can be set in the range of 0.5 to 10 µm. As a method of patterning such resinous light-shielding portion, methods such as a photolithography method and a printing method that are generally used can be used.

The light-shielding portions may be ones formed on the surface of the side at which the cell culture patterning layer which will be detailed later is formed, or ones formed on the opposite surface.

In the case of forming the light-shielding portions, a primer layer may be formed between the cell culture patterning layer and the light-shielding portions. The effect and function of this primer layer are not necessarily clear, but would be as follows: the primer layer exhibits a function of preventing the diffusion of impurities from the light-shielding portions and openings which are present between the light-shielding portions, the impurities being factors for inhibiting the decomposition or denaturation of the cell adhesive material in the photocatalyst-containing cell adhesive layer by action of the photocatalyst, in particular, residues generated when the light-shielding portions are patterned, or metal, metal ion impurities, or the like. Accordingly, the formation of the primer layer makes it possible to decompose or denature the cell adhesive material with high sensitivity in the energy irradiating process, which will detailed later, so that a cell adhesion portion and a cell adhesion-inhibiting portion are formed in a highly precise pattern form.

The primer layer in the embodiment is a layer for preventing the effect of the photocatalyst from being affected by the impurities present inside not only the light-shielding portions but also the openings made between the light-shielding portions. It is therefore preferred to form the primer layer over the entire surface of the light-shielding portions plus the openings.

The primer layer in the invention is not limited to any special structure if the primer layer is formed not to bring the light-shielding portions and the cell culture patterning layer into contact with each other.

A material that forms the primer layer, though not particularly restricted, is preferably an inorganic material that is not likely to be decomposed by action of the photocatalyst. Specifically, amorphous silica can be cited. When such amorphous silica is used, a precursor of the amorphous silica is preferably a silicon compound that is represented by a general formula, $SiX_4$, X being halogen, methoxy group, ethoxy group, acetyl group or the like, silanol that is a hydrolysate thereof, or polysiloxane having an average molecular weight of 3000 or less.

A film thickness of the primer layer is preferably in the range of 0.001 to 1 µm and particularly preferably in the range of 0.001 to 0.1 µm.

It is preferred that on the base material a position-detecting mark is formed at a given location thereof. This makes the positioning of the base material easy in the energy irradiating process or the cell-containing liquid applying process, which will be detailed later to make it possible to form the cell adhesion-inhibiting portion at a given location or applying the cell-containing liquid selectively and highly precisely only onto the cell adhesion portion. No special limitation is imposed on such position-detecting mark if the mark can be detected in the energy irradiating process or the cell-containing liquid applying process. Thus, the mark may be the same mark as is ordinarily used for the positioning of substrates, or the like.

(Photocatalyst-Containing Cell Adhesive Layer)

The following will describe the photocatalyst-containing cell adhesive layer formed in the present process. The photocatalyst-containing cell adhesive layer is a layer comprising at least a photocatalyst and a cell adhesive material which has cell adhesive properties and is decomposed or denatured by action of the photocatalyst on the basis of energy irradiation. In the embodiment, the method for forming the layer is not specially limited if the method makes the formation of the layer possible. For example, the layer can be formed by applying a coating solution for forming a photocatalyst-containing cell adhesive layer which comprises the photocatalyst and the cell adhesive material by the above-mentioned applying method.

For example, when concave portions are made in the base material as describe above, it is possible to use: a casting process of dropping down the coating solution for forming a photocatalyst-containing cell adhesive layer into the concave portions, and drying the solution so as to form the photocatalyst-containing cell adhesive layer; an adsorbing process of dropping down the coating solution for forming a photocatalyst-containing cell adhesive layer into the concave portions of the base material, and washing the surface after a given time; or some other process.

The film thickness of the photocatalyst-containing layer is appropriately selected in accordance with the kind of the cell culture substrate and other factors, and may be usually from about 0.01 to 1.0 µm, preferably from about 0.1 to 0.3 µm.

The following will describe each of the materials used in the photocatalyst-containing cell adhesive layer.

a. Cell Adhesive Material

First, the cell adhesive material used in the photocatalyst-containing cell adhesive layer formed in the embodiment is described. About the cell adhesive material, the kind thereof and others are not specially limited if the material has cell adhesive properties and is decomposed or denatured by action of a photocatalyst on the basis of energy irradiation. The wording "the material has cell adhesive properties" referred to herein means that the material adheres well to cells. When, for example, adhesive properties of the material to cells are different in accordance with the kinds of the cells, the wording means that the material adheres well onto target one out of the cells.

The cell adhesive material used in the present embodiment has such cell adhesive properties and can be decomposed or denatured by action of the photocatalyst on the basis of energy irradiation such as to lose the cell adhesive properties or change to one that has the cell adhesion inhibiting properties that inhibit to adhere to cells.

As such materials having the cell adhesive properties, there are two kinds, one being materials having the cell adhesive properties owing to physicochemical characteristics and the other being materials having the cell adhesive properties owing to biochemical characteristics.

As physicochemical factors that determine the cell adhesive properties of materials having the cell adhesive properties owing to the physicochemical characteristics, the surface free energy, the electrostatic interaction and the like can be cited. For instance, in the case of the cell adhesive properties being determined by the surface free energy of the material, when the material has the surface free energy in a predetermined range, the adhesive properties between the cells and the material becomes good, and when it deviates from the above range the adhesive properties between the cells and material decreases. As such changes of the cell adhesive properties due to the surface free energy, experimental results such as shown in Data, for instance, CMC Publishing Co., Ltd. "Biomaterial no Saisentan", Yoshito IKADA (editor), p. 109, lower part are known. As materials having the cell adhesive properties owing to such a factor, for instance, hydrophilic polystyrene, poly (N-isopropyl acrylamide) and the like can be cited. When such a material is used, by action of the photocatalyst on the basis of energy irradiation, for instance, a functional group on a surface of the material is substituted, decomposed or the like to cause a change in the surface free energy, resulting in one that does not have the cell adhesive properties or one that has the cell adhesion inhibiting properties.

When the adhesive properties between cells and a material is determined owing to the electrostatic interaction or the like, for instance, the cell adhesive properties can be determined owing to an amount of positive electric charges and the like that the material has. As materials having the cell adhesive properties owing to such electrostatic interaction, basic polymers such as polylysine, basic compounds such as aminopropyltriethoxysilane, N-(2-aminoethyl)-3-aminopropyltrimethoxysilane and condensates and the like including these can be cited. When such materials are used, by action of the photocatalyst on the basis of energy irradiation, the above-mentioned materials are decomposed or denatured, thereby, for instance, an amount of positive electric charges present on a surface can be altered, resulting in one that does not have the cell adhesive properties or one that has the cell adhesion inhibiting properties.

As materials having the cell adhesive properties owing to the biological characteristics, ones that are good in the adhesive properties with particular cells, ones that are good in the adhesive properties with many cells, or the like can be cited. Specifically, fibronectin, laminin, tenascin, vitronectin, RGD (arginine-glycine-asparagine acid) sequence containing peptide, YIGSR (tyrosine-isoleucine-glycine-serine-arginine) sequence containing peptide, collagen, atelocollagen, gelatin, albumin, γ-globulin, and the like can be cited. When such materials are used, by action of the photocatalyst on the basis of energy irradiation, for instance, a structure of the material is partially destroyed, a principal chain is destroyed or the like, resulting in one that does not have the cell adhesive properties or one that has the cell adhesion inhibiting properties.

The amount of the cell adhesive material is varied in accordance with the kind of the material, or the like. Usually, the content by percentage of the cell adhesive material in the photocatalyst-containing cell adhesive layer is preferably from 0.01 to 95% by weight, more preferably from 1 to 10% by weight. This makes it possible to render the region comprising the cell adhesive material a region good in cell adhesive properties.

b. Photocatalyst

The following will describe the photocatalyst comprised in the photocatalyst-containing cell adhesive layer formed in the present embodiment. The photocatalyst is not limited to any special kind if the cell adhesive material can be decomposed or denatured by action of this photocatalyst on the basis of energy irradiation.

An action mechanism of the photocatalyst typical in titanium oxide described below is not necessarily clear. However, it can be considered that a carrier generated by irradiation of light directly reacts with a nearby compound or, owing to an active oxygen species generated under the presence of oxygen, water, a chemical structure of an organic material is caused to change. In the invention, the carrier is considered to affect on the cell adhesive material described above.

As the photocatalyst that can be used in the present embodiment, specifically, for instance, titanium dioxide ($TiO_2$), zinc oxide (ZnO), tin oxide ($SnO_2$) strontium titanate ($SrTiO_3$), tungsten oxide ($WO_3$), bismuth oxide ($Bi_2O_3$) and iron oxide ($Fe_2O_3$) that are known as photo-semiconductors can be cited. These can be used singularly or in combination of at least two kinds.

In the present embodiment, in particular, titanium dioxide, owing to a large band gap, chemical stability, non-toxicity, and easy availability, can be preferably used. There are two types of titanium dioxide, anatase type and rutile type, and both can be used in the invention; however, the anatase type titanium dioxide is more preferable. An excitation wavelength of the anatase type titanium dioxide is 380 nm or less.

As such anatase type titanium dioxide, for instance, an anatase titania sol of hydrochloric acid deflocculation type (trade name: STS-02, manufactured by ISHIHARA SANGYO KAISHA, LTD., average particle diameter: 7 nm, and trade name: ST-KO1, manufactured by ISHIHARA SANGYO KAISHA, LTD.), an anatase titania sol of nitric acid deflocculation type (tradename: TA-15, manufactured by NISSAN CHEMICAL INDUSTRIES LTD., average particle diameter: 12 nm) and the like can be cited.

The smaller is a particle diameter of the photocatalyst, the better, because a photocatalyst reaction is caused more effectively. An average particle diameter of the photocatalyst is preferably 50 nm or less, and one having an average particle diameter of 20 nm or less can be particularly preferably used.

The content by percentage of the photocatalyst in the photocatalyst-containing cell adhesive layer formed in the embodiment can be set into a value from 5 to 95% by weight, preferably from 10 to 60% by weight, more preferably from 20 to 40% by weight. This makes it possible to decompose or denature the cell adhesive material inside the energy-irradiated region in the photocatalyst-containing cell adhesive layer in the energy irradiating process, which will be detailed later.

The photocatalyst used in the embodiment is preferably a photocatalyst low in cell adhesive properties. This makes it possible to use, as a region low in cell adhesive properties, the region where the cell adhesive material is decomposed or the like so that the photocatalyst is exposed.

c. Others

In the present embodiment, the photocatalyst-containing cell adhesive layer may comprise, besides the cell adhesive material and the photocatalyst, a binder for improving the strength or resistance thereof, or the like if necessary. In the embodiment, it is particularly preferred to use, as the binder, a material having cell adhesion-inhibiting properties for inhibiting adhesion onto cells at least after the material is irradiated with energy. This makes it possible to make low the cell adhesive properties of the region irradiated with the energy in the energy irradiating process, which will be detailed later. The material may be, for example, a material having cell adhesion-inhibiting properties from before the material is irradiated with energy, or a material coming to have cell adhesion-inhibiting properties by action of a photocatalyst on the basis of energy irradiation.

In the embodiment, the content by percentage of the binder in the photocatalyst-containing cell adhesive layer is preferably from 5 to 95% by weight, more preferably from 40 to 90% by weight, even more preferably from 60 to 80% by weight.

(2) Second Embodiment

The patterning substrate formed according to the second embodiment is a patterning substrate comprising a base material, and a cell culture patterning layer which is formed on the base material and has a photocatalyst-containing cell adhesion-inhibiting material layer comprising at least a photocatalyst and a cell adhesion-inhibiting material which has cell adhesion-inhibiting properties of inhibiting adhesion onto cells and is decomposed or denatured by action of the photocatalyst on the basis of energy irradiation.

The photocatalyst-containing cell adhesion-inhibiting material layer formed in the embodiment comprises therein the photocatalyst; therefore, in the energy irradiating process, which will be detailed later, at the time of irradiating energy, the cell adhesion-inhibiting material in the layer can be decomposed or denatured by action of the photocatalyst. It is therefore unnecessary to form a layer comprising any photocatalyst separately in the cell culture patterning layer. Thus, the cell culture patterning layer can be rendered a single layer. This is preferred from the viewpoint of production efficiency and the like. If necessary, the cell culture patterning layer may be formed to comprise a layer other than the photocatalyst-containing cell adhesion-inhibiting layer.

The following will describe the photocatalyst-containing cell adhesion-inhibiting material layer formed in the present process. The base material used in the present process may be the same as used in the first embodiment. Thus, description thereof is omitted herein.

(Photocatalyst-Containing Cell Adhesion-Inhibiting Material Layer)

The photocatalyst-containing cell adhesion-inhibiting material layer formed in the process is a layer comprising at least a photocatalyst and a cell adhesion-inhibiting material which has cell adhesion-inhibiting properties of inhibiting adhesion onto cells and is decomposed or denatured by action of the photocatalyst on the basis of energy irradiation. In the embodiment, the method for forming the layer, or the like is not specially limited if the method makes the formation of the layer possible. For example, the layer can be formed by applying a coating solution for forming a photocatalyst-containing cell adhesion-inhibiting material layer which comprises the photocatalyst and the cell adhesion-inhibiting material by the above-mentioned applying method, or the like.

For example, when concave portions are made in the base material as describe above, it is possible to use: a casting process of dropping down the coating solution for forming a photocatalyst-containing cell adhesion-inhibiting material layer into the concave portions, and drying the solution so as to form the photocatalyst-containing cell adhesion-inhibiting material layer; an adsorbing process of dropping down the coating solution for forming a photocatalyst-containing cell adhesion-inhibiting material layer into the concave portions of the base material, and washing the surface after a given time; or some other process.

The film thickness of the photocatalyst-containing layer is appropriately selected in accordance with the kind of the cell culture substrate and other factors, and may be usually from about 0.01 to 1.0 μm, preferably from about 0.1 to 0.3 μm.

The following will describe each of the materials used in the photocatalyst-containing cell adhesion-inhibiting layer formed in the embodiment. The photocatalyst used in the photocatalyst-containing cell adhesion-inhibiting layer is the same as used in the first embodiment. Thus, description thereof is omitted herein.

a. Cell Adhesion-Inhibiting Material

First, the cell adhesion-inhibiting material used in the photocatalyst-containing cell adhesion-inhibiting material layer formed in the embodiment is described.

About the cell adhesion-inhibiting material, the kind thereof and others are not specially limited if the material has cell adhesion-inhibiting properties of inhibiting adhesion onto cells and is decomposed or denatured by action of a photocatalyst on the basis of energy irradiation.

Here, the wording "having the cell adhesion-inhibiting properties" means having a property that inhibits cells from adhering to the cell adhesion-inhibiting material, and, when cell adhesive properties are different depending on the kind of cells and the like, means to have the property of inhibiting from adhering with a target cell.

As the cell adhesion-inhibiting material used in the present embodiment, one that has such cell adhesion-inhibiting properties and can be decomposed or denatured by an action of the photocatalyst on the basis of energy irradiation to lose the cell adhesion-inhibiting properties or to become good in the cell adhesive properties can be used.

As such cell adhesion-inhibiting material, materials high in, for instance, the hydration ability can be used. When the material high in the hydration ability is used, water molecules gather in the vicinity of the cell adhesion-inhibiting material to form a hydrated layer. Normally, such material high in the hydration ability is higher in an adhesiveness with water molecules than that with cells; accordingly, cells cannot adhere to the material high in the hydration ability, resulting in one low in the cell adhesive properties. Here, "the hydration ability" means a property of hydrolyzing with water molecules, and "the hydration ability being high" means that it can readily hydrolyze with water molecules.

As materials that are high in the hydration ability and can be used as the cell adhesion-inhibiting material, for instance, polyethylene glycol, amphoteric ion materials having a betaine structure or the like, and phosphatide-containing materials and the like can be cited. In the case of such a material being used as the cell adhesion-inhibiting material, when energy is irradiated in an energy irradiating process to be described later, owing to an action of the photocatalyst, the cell adhesion-inhibiting material is decomposed, denatured or the like, the hydrated layer on a surface comes off, and thereby the cell adhesion-inhibiting material is rendered one that does not have the cell adhesion-inhibiting properties.

In the present embodiment, as the cell adhesion-inhibiting material, a surfactant having a water repellent or oil repellent organic group that can be decomposed by an action of the photocatalyst also can be used. As such surfactant, hydrocarbons base surfactants such as the respective series of NIKKO L, BL, BC, BO, and BB manufactured by Nikko Chemicals Co., Ltd., and fluorine base or silicone base nonionic surfactants such as ZONYL FSN and FSO manufacture by Du Pont Kabushiki Kaisya, Surflon S-141 and 145 manufactured by ASAHI GLASS CO., LTD., Megaface F-141 and 144 manufactured by DAINIPPON INK AND CHEMICALS, Inc., FTERGENT F-200 and F251 manufactured by NEOS, UNIDYNE DS-401 and 402 manufactured by DAIKIN INDUSTRIES, Ltd., and Fluorad FC-170 and 176 manufactured by 3M can be cited, and furthermore cationic surfactants, anionic surfactants and amphoteric surfactants also can be used.

In the case of such a material being used as the cell adhesion-inhibiting material to form the photocatalyst-containing cell adhesion-inhibiting material layer, the cell adhesion-inhibiting material is distributed unevenly on a surface. Thereby, the water repellency or oil repellency of the surface can be made higher; accordingly, one small in the interaction with cells and low in the cell adhesive properties can be obtained. Furthermore, when energy is irradiated on the layer, by action of the photocatalyst, the cell adhesion-inhibiting material is readily decomposed to expose the photocatalyst, resulting in one that does not have the cell adhesion-inhibiting properties.

In the present embodiment, as the cell adhesion-inhibiting material, one that can be improved in the cell adhesive properties by action of the photocatalyst on the basis of energy irradiation is particularly preferably used. As such cell adhesion-inhibiting materials, for instance, materials having the oil repellency or water repellency can be cited.

In the case of, as the cell adhesion-inhibiting material, a material having the water repellency or the oil repellency being used, owing to the water repellency or the oil repellency of the cell adhesion-inhibiting material, one in which an interaction such as a hydrophobic interaction between cells and the cell adhesion-inhibiting material is small and the cell adhesive properties are low can be obtained.

As a material having such water repellency or the oil repellency, for instance, one where a skeleton has such a high bond energy that cannot be decomposed by action of the photocatalyst and that has a water repellent or oil repellent organic substitution group that can be decomposed by action of the photocatalyst can be cited.

As one that has the skeleton having such high bond energy that cannot be decomposed by action of the photocatalyst and the water repellent or oil repellent organic substitution group that can be decomposed by action of the photocatalyst, for instance, (1) organopolysiloxane that exhibits large strength by hydrolyzing or polycondensating chloro, alkoxysilane or the like owing to a sol-gel reaction and the like, and (2) organopolysiloxane or the like in which reactive silicones are crosslinked can be cited.

In the case of the (1), it is preferable to be organopolysiloxane that is a hydrolysis condensate or cohydrolysis condensate of at least one kind of silicon compounds expressed by a general formula:

$$Y_nSiX_{(4-n)}$$

(Here, Y denotes an alkyl group, fluoroalkyl group, vinyl group, amino group, phenyl group or epoxy group, or organic groups including these, and X denotes an alkoxyl group, acetyl group or halogen. n is an integer of 0 to 3). The number of carbons of the group expressed with Y is preferably in the range of 1 to 20, and the alkoxy group expressed with X is preferably a methoxy group, ethoxy group, propoxy group or butoxy group.

As the organic groups, in particular, polysiloxane containing a fluoroalkyl group can be preferably used. Specifically, a hydrolysis condensate or cohydrolysis condensate of at least one kind of fluoroalkylsilanes below can be cited. Ones generally known as the fluorinated silane coupling agents can be used.

$CF_3(CF_2)_3CH_2CH_2Si(OCH_3)_3$;
$CF_3(CF_2)_5CH_2CH_2Si(OCH_3)_3$;
$CF_3(CF_2)_7CH_2CH_2Si(OCH_3)_3$;
$CF_3(CF_2)_9CH_2CH_2Si(OCH_3)_3$;
$(CF_3)_2CF(CF_2)_4CH_2CH_2Si(OCH_3)_3$;
$(CF_3)_2CF(CF_2)_6CH_2CH_2Si(OCH_3)_3$;
$(CF_3)_2CF(CF_2)_8CH_2CH_2Si(OCH_3)_3$;
$CF_3(C_6H_4)C_2H_4Si(OCH_3)_3$;
$CF_3(CF_2)_3(C_6H_4)C_2H_4Si(OCH_3)_3$;
$CF_3(CF_2)_5(C_6H_4)C_2H_4Si(OCH_3)_3$;
$CF_3(CF_2)_7(C_6H_4)C_2H_4Si(OCH_3)_3$;
$CF_3(CF_2)_3CH_2CH_2SiCH_3(OCH_3)_2$;
$CF_3(CF_2)_5CH_2CH_2SiCH_3(OCH_3)_2$;
$CF_3(CF_2)_7CH_2CH_2SiCH_3(OCH_3)_2$;
$CF_3(CF_2)_9CH_2CH_2SiCH_3(OCH_3)_2$;
$(CF_3)_2CF(CF_2)_4CH_2CH_2SiCH_3(OCH_3)_2$;
$(CF_3)_2CF(CF_2)_6CH_2CH_2Si CH_3(OCH_3)_2$;
$(CF_3)_2CF(CF_2)_8CH_2CH_2Si CH_3(OCH_3)_2$;
$CF_3(C_6H_4)C_2H_4SiCH_3(OCH_3)_2$;
$CF_3(CF_2)_3(C_6H_4)C_2H_4SiCH_3(OCH_3)_2$;
$CF_3(CF_2)_5(C_6H_4)C_2H_4SiCH_3(OCH_3)_2$;
$CF_3(CF_2)_7(C_6H_4)C_2H_4SiCH_3(OCH_3)_2$;
$CF_3(CF_2)_3CH_2CH_2Si(OCH_2CH_3)_3$;
$CF_3(CF_2)_5CH_2CH_2Si(OCH_2CH_3)_3$;
$CF_3(CF_2)_7CH_2CH_2Si(OCH_2CH_3)_3$;
$CF_3(CF_2)_9CH_2CH_2Si(OCH_2CH_3)_3$;
$CF_3(CF_2)_7SO_2N(C_2H_5)C_2H_4CH_2Si(OCH_3)_3$

When polysiloxane containing such a fluoroalkyl group is used as the cell adhesion-inhibiting material, one high in the water repellency or oil repellency can be formed, resulting in rendering one small in the interaction with cells and low in the cell adhesive properties. Furthermore, when energy is irradiated on such a material, readily, fluorine and the like can be removed and an OH group and the like can be introduced on a surface to render the interaction with cells larger; accordingly, the cell adhesive properties can be made good.

As the reactive silicone according to the (2), compounds having a skeleton expressed by a general formula below can be cited.

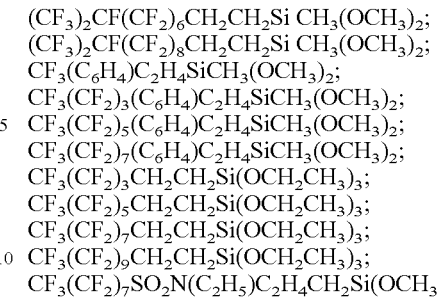

In the above general formula, n denotes an integer of 2 or more, $R^1$ and $R^2$ each represents a substituted or nonsubstituted alkyl group, alkenyl group, aryl group or cyanoalkyl group having 1 to 20 carbons, and a vinyl, phenyl and halogenated phenyl occupy 40% or less by mole ratio to a total mole. Furthermore, one in which $R^1$ and $R^2$ each is a methyl group is preferable because the surface energy is the lowest, and a methyl group is preferably contained 60% or more by mole ratio. Still furthermore, a chain terminal or side chain has at least one or more reactive group such as a hydroxyl group in a molecular chain.

Together with the organopolysiloxane, a stable organosilicium compound that does not cause a crosslinking reaction such as dimethylpolysiloxane may be blended separately.

When such reactive silicone is used, one high in the water repellency or oil repellency can be obtained; that is, one small in the interaction with cells and low in the cell adhesive properties can be obtained. Furthermore, when energy is irradiated on such a material, readily, a substituent group can be removed and an OH group and the like can be introduced on a surface to render the interaction with cells larger; accordingly, the cell adhesive properties can be made good.

In the case of using as the cell adhesion-inhibiting material a polysiloxane or reactive silicone as described above, the region irradiated with energy in the energy irradiating process can be rendered a region having hydrophilicity, and the cell adhesion-inhibiting portion not irradiated with the energy can be rendered a region having water repellency. This gives an advantage that when a cell-containing liquid is applied by the region-selecting applying method in the cell-containing liquid applying process, which will be detailed later, cells can be caused to adhere in a more highly precise pattern form since the cells do not adhere onto the cell adhesion-inhibiting portion but the cells adhere only onto the cell adhesion portion.

The above-mentioned word "hydrophilicity" means a small contact angle with water, and the wordings "water repellency" means a large contact angle with water. Specifically, in the region not irradiated with energy, that is, the cell adhesion-inhibiting portion having water repellency, the contact angle with water is preferably 100° or more, more preferably from 110 to 130°. If the contact angle with water is smaller than this range, the cell-containing liquid applied by the region-selecting applying method in the cell-containing liquid applying process, which will be detailed later, may adhere onto the cell adhesion-inhibiting portion. The water repellency and oil repellency of the surface can be made higher by, for example, a method described in "Ogawa et al., Japanese Journal of Applied Physics P2, 32, (1993) L614-", for instance, a method of subjecting a base material to reduced-pressure plasma treatment to make fine irregularities in the base material, and further applying a water repellent and oil repellent material onto the base material. In the case of using such a surface, the contact angle of the cell adhesion-inhibiting portion with water can be made as high as about 160°.

In the region irradiated with energy, that is, the cell adhesion portion having hydrophilicity, the contact angle with water is preferably 50° or lower, more preferably from 10 to 40°, even more preferably from 15 to 30°. If the contact angle with water is larger than the range, the cell adhesion portion repels the cell-containing liquid applied by the region-selecting applying method in the cell-containing liquid applying process, which will be detailed later, so that cells may not be caused to adhere onto the portion.

The contact angle with water referred to herein is a result obtained by using a contact angle measuring device (CA-Z model, manufactured by Kyowa Interface Science Co., Ltd.) to measure the contact angle of the material with water or a liquid having a contact angle equivalent to that of water (after 30 seconds from the time when droplets of the liquid are dropped down from its micro syringe), or a value obtained from a graph prepared from the result.

The content by percentage of the cell adhesion-inhibiting material in the photocatalyst-containing cell adhesion-inhibiting material layer is preferably from 0.01 to 95% by weight, more preferably from 1 to 10% by weight. This makes it possible to render the region comprising the cell adhesion-inhibiting material a region low in cell adhesive properties.

The cell adhesion-inhibiting material preferably has surface activity. This makes it possible that, for example, when a coating solution, for forming the photocatalyst-containing cell adhesion-inhibiting material layer, which comprises the cell adhesion-inhibiting material is applied, then dried and the like, the ratio of the material distributed unevenly in the surface of the coating film becomes high so that good cell adhesion-inhibiting properties can be obtained.

(Others)

The photocatalyst-containing cell adhesion-inhibiting material layer in the present embodiment may comprise such as a binder in accordance with properties required for a coating liquid for patterning substrate, for example, the coating property for forming this layer, and the strength or resistance of the layer. The cell adhesion-inhibiting material may fulfill a part of the binder.

The binder may be, for example, a compound having a high bonding energy such that the main skeleton thereof is not decomposed by action of the above-mentioned photocatalyst. A specific example thereof is a polysiloxane having no organic substituent or having one or more organic substituents to such a degree that no effect is produced on the cell adhesive property. The polysiloxane can be obtained by hydrolyzing or polycondensing tetramethoxysilane, tetraethoxysilane or the like.

In the embodiment, the content by percentage of the binder in the photocatalyst-containing cell adhesion-inhibiting material layer is preferably from 5 to 95% by weight, more preferably from 40 to 90% by weight, even more preferably from 60 to 80% by weight. This makes it possible to exhibit various properties.

In the embodiment, it is particularly preferred that the photocatalyst-containing cell adhesion-inhibiting material layer comprises a cell adhesive material having cell adhesive properties at least after the material is irradiated with energy. This makes it possible that the photocatalyst-containing cell adhesion-inhibiting material layer makes the cell adhesive properties of the region irradiated with the energy better in the energy irradiating process, which will be detailed later. The cell adhesive material may be a material used as the above-mentioned binder, or a material used independently of the binder. The cell adhesive material may be, for example, a material having good cell adhesive properties even before the material is irradiated with energy, or a material coming to have good cell adhesive properties by action of a photocatalyst on the basis of energy irradiation. The wording "a material having cell adhesive properties" referred to herein means that the material adhere well onto cells. When adhesive properties of the material to cells are different in accordance with the kinds of the cells or the like, the wording means that the material adheres well onto target one out of the cells.

In the present embodiment, as far as the cell adhesive material has good cell adhesive properties at least after energy is irradiated, it may be one of which cell adhesive properties are made good owing to physical interactions such as an hydrophobic interaction, electrostatic interaction, hydrogen bonding, van der Waals force and the like or owing to biological characteristics.

In the embodiment, the content by percentage of the cell adhesive material in the photocatalyst-containing cell adhesion-inhibiting material layer is preferably from 0.01 to 95% by weight, more preferably from 1 to 10% by weight. This makes it possible that the photocatalyst-containing cell adhesion-inhibiting material layer makes the cell adhesive properties of the region irradiated with energy better in the energy irradiating process, which will be detailed later. In the case of using, as the cell adhesive material, a material having good cell adhesive properties even before the material is irradiated with energy, it is preferred that the cell adhesive material is contained to such a degree that the cell adhesion-inhibiting properties of the cell adhesion-inhibiting material is not inhibited in the region not irradiated with energy.

(3) Third Embodiment

The patterning substrate obtained according to the third embodiment of the present process is a patterning substrate comprising a base material, and a cell culture patterning layer which is formed on the base material and has a photocatalyst-containing layer comprising at least a photocatalyst and a cell adhesive layer formed on the photocatalyst-containing layer, wherein the cell adhesive layer comprises at least a cell adhesive material which has cell adhesive properties and is decomposed or denatured by action of the photocatalyst on the basis of energy irradiation.

In the embodiment, the cell culture patterning layer has the cell adhesive layer and the photocatalyst-containing layer; therefore, in the energy irradiating process, which will be detailed later, at the time of irradiating energy, the cell adhesive material in the cell adhesive layer can be decomposed or denatured by action of the photocatalyst comprised in the photocatalyst-containing layer, so that a cell adhesion-inhibiting portion can be formed.

According to the present embodiment, the cell adhesive layer is formed on the photocatalyst-containing layer; therefore, at the time of culturing cells, the cells do not contact the photocatalyst directly, thereby producing an advantage of making low the possibility that the cells are affected by the photocatalyst with the passage of time.

The following will describe the cell adhesive layer and the photocatalyst-containing layer in the cell culture patterning layer formed according to the embodiment. The base material used in the embodiment may be the same as described in the first embodiment. Thus, description thereof is omitted herein.

(Cell Adhesive Layer)

First, the cell adhesive layer comprised in the cell culture patterning layer formed in the embodiment is described. The cell adhesive layer is a layer formed on the photocatalyst-containing layer which will be detailed later, and is a layer comprising at least a cell adhesive material which has cell adhesive properties and is decomposed or denatured by action of a photocatalyst on the basis of energy irradiation.

In the embodiment, the method for forming the layer or the like is not specially limited if the method makes the formation of the layer possible. For example, the layer can be formed by applying a coating solution for forming a cell adhesive layer, which comprises the cell adhesive material by the above-mentioned applying method, or other method.

When concave portions are made in the base material as describe above, it is possible to use: a casting process of forming a photocatalyst-containing layer, which will be detailed later, onto the concave portions in the base material, dropping down the coating solution for forming a cell adhesive layer, into the concave portions, and drying the solution so as to form the cell adhesive layer; an adsorbing process of forming a photocatalyst-containing layer, which will be detailed later, onto the concave portions in the base material, dropping down the coating solution for forming a cell adhesive layer, into the concave portions, and washing the surface after a given time; or some other process.

The film thickness of such cell adhesive layer is appropriately selected in accordance with the kind of the cell culture substrate and other factors, and may be usually from about 0.001 to 1.0 μm, preferably from about 0.005 to 0.1 μm.

Specific examples of the cell adhesive material used in the cell adhesive layer formed in the embodiment may be those equivalent to those of the cell adhesive material used in the photocatalyst-containing cell adhesive layer in the first embodiment. Thus, detailed description thereof is omitted herein. It is preferred that the cell adhesive layer in the embodiment also comprises a material having the cell adhesion-inhibiting properties described about the photocatalyst-containing cell adhesive layer in the first embodiment. This makes it possible to make the cell adhesive properties of the region irradiated with energy low in the energy irradiating process.

(Photocatalyst-Containing Layer)

The following will describe the photocatalyst-containing layer comprised in the cell culture patterning layer formed in the embodiment. The photocatalyst-containing layer is not limited to any special kind if the layer is a layer comprising a photocatalyst. The layer may be a layer made only of the photocatalyst, or a layer comprising one or more different components, such as a binder, also.

The photocatalyst used in the embodiment may be the same as used in the photocatalyst-containing cell adhesive layer in the first embodiment. In the embodiment also, titanium oxide is particularly preferred.

It is advantageous from the viewpoint of costs to use the photocatalyst-containing layer made only of a photocatalyst since the efficiency of decomposing or denaturing the cell adhesive material in the cell adhesive layer is improved to make the time for the treatment shorter or the like. On the other hand, the use of the photocatalyst-containing layer made of a photocatalyst and a binder gives an advantage of making the formation of the photocatalyst-containing layer easy.

An example of the method for forming the photocatalyst-containing layer made only of a photocatalyst may be a vacuum film-forming method such as sputtering, CVD or vacuum vapor deposition. The formation of the photocatalyst-containing layer by the vacuum film-forming method makes it possible to render the layer a homogeneous photocatalyst-containing layer made only of a photocatalyst, thereby decomposing or denaturing the cell adhesive material homogeneously, and further thereby making the decomposition or denaturation of the cell adhesive material more effective in this case than in the case of using a binder also since the layer is made only of the photocatalyst. When concave portions are formed on the base material mentioned above, the photocatalyst-containing layer can be formed by the above-mentioned method.

Another example of the method for forming the photocatalyst-containing layer made only of a photocatalyst, is the following method: in the case that the photocatalyst is, for example, titanium dioxide, amorphous titania is formed on the base material and next fired so as to phase-change the titania to crystalline titania. The amorphous titania used in this case can be obtained, for example, by hydrolysis or dehydration condensation of an inorganic salt of titanium, such as titanium tetrachloride or titanium sulfate, or hydrolysis or dehydration condensation of an organic titanium compound, such as tetraethoxytitanium, tetraisopropoxytitanium, tetra-n-propoxytitanium, tetrabutoxytitanium or tetramethoxytitanium, in the presence of an acid. Next, the resultant is fired at 400 to 500° C. so as to be denatured to anatase type titania, and fired at 600 to 700° C. so as to be denatured to rutile type titania.

In the case of using a binder together with the above-mentioned photocatalyst, the binder is preferably a binder having a high bonding energy, wherein its main skeleton is not decomposed by photoexcitation of the photocatalyst. Examples of such a binder include the organopolysiloxanes described in the above-mentioned item "Cell Adhesive Layer".

In the case of using such an organopolysiloxane as the binder, the photocatalyst-containing layer can be formed by dispersing a photocatalyst, the organopolysiloxane as the binder, and optional additives if needed into a solvent to prepare a coating liquid, and applying this coating liquid onto the base material. The used solvent is preferably an alcoholic based organic solvent such as ethanol or isopropanol. The application can be performed by a known coating method such as spin coating, spray coating, dip coating, roll coating, or bead coating. When the coating liquid contains an ultraviolet curable component as the binder, the photocatalyst-containing layer can be formed by curing the coating liquid through the irradiation of ultraviolet rays onto the liquid.

When concave portions are formed on the base material mentioned above, it is allowable to perform such as a casting method of dropping down the above-mentioned coating liquid into the concave portions and then drying the liquid to form the photocatalyst-containing layer.

As the binder, an amorphous silica precursor can be used. This amorphous silica precursor is preferably a silicon compound represented by the general formula $SiX_4$, wherein X are a halogen, a methoxy group, an ethoxy group, an acetyl group or the like; a silanol which is a hydrolyzate thereof; or a polysiloxane having an average molecular weight of 3000 or less.

Specific examples thereof include such as tetraethoxysilane, tetraisopropoxysilane, tetra-n-propoxysilane, tetrabutoxysilane, and tetramethoxysilane. In this case, the photocatalyst-containing layer can be formed by dispersing the amorphous silica precursor and particles of a photocatalyst homogeneously into a non-aqueous solvent, hydrolyzing the precursor with water content in the air to form a silanol onto a transparent base material, and then subjecting the silanol to dehydration polycondensation at room temperature. When the dehydration polycondensation of the silanol is performed at 100° C. or higher, the polymerization degree of the silanol increases so that the strength of the film surface can be improved. A single kind or two or more kinds of this binding agent may be used.

The content by percentage of the photocatalyst in the photocatalyst-containing layer is from 5 to 60% by weight, preferably from 20 to 40% by weight. The thickness of the photocatalyst-containing layer is preferably from 0.05 to 10 μm.

Besides the above-mentioned photocatalyst and binder, the surfactant and so on described in the above-mentioned item "Cell Adhesive Layer" can be incorporated into the photocatalyst-containing layer.

In the present embodiment, one or more light-shielding portions may be formed on the photocatalyst-containing layer, as described above. According to this, in the energy irradiating process, which will be detailed later, when the entire surface of the cell adhesive layer is irradiated with energy, the cell adhesive material contained in regions of the cell adhesive layer other than the regions thereof on which the light-shielding portions are formed can be decomposed or denatured without exciting the photocatalyst in the regions on which the light-shielding portions are formed. This case has an advantage that the direction in which the energy is irradiated is not particularly limited since the photocatalyst in the regions where light-shielding portions are formed is not excited.

Such light-shielding portions may be the same as described in the item "Base Material" in the first embodiment. Thus, detailed description thereof is omitted herein.

(4) Fourth Embodiment

The patterning substrate formed in the fourth embodiment of the present process is a patterning substrate comprising a base material, and a cell culture patterning layer which is formed on the base material and has a photocatalyst-containing layer comprising at least a photocatalyst and a cell adhesion-inhibiting material layer formed on the photocatalyst-containing layer, wherein the cell adhesion-inhibiting material layer comprises a cell adhesion-inhibiting material which has cell adhesion-inhibiting properties of inhibiting adhesion onto the cells and is decomposed or denatured by action of the photocatalyst on the basis of energy irradiation.

In the embodiment, the cell culture patterning layer has the cell adhesion-inhibiting material layer and the photocatalyst-containing layer; therefore, in the energy irradiating process, which will be detailed later, at the time of irradiating energy, the cell adhesion-inhibiting material in the cell adhesion-inhibiting material layer can be decomposed or denatured by action of the photocatalyst comprised in the photocatalyst-containing layer, so that a cell adhesion portion can be formed.

The following will describe the cell adhesion-inhibiting material layer in the cell culture patterning layer formed in the embodiment. The base material used in the embodiment may be the same as described in the first embodiment. The photocatalyst-containing layer may be the same as described in the third embodiment. Thus, description thereof is omitted herein.

(Cell Adhesion-Inhibiting Material Layer)

The cell adhesion-inhibiting material layer formed in the embodiment is a layer formed on the photocatalyst-containing layer, and is not limited to any special kind if the layer is a layer comprising a cell adhesion-inhibiting material which has cell adhesion-inhibiting properties of inhibiting adhesion onto cells and is decomposed or denatured by action of a photocatalyst on the basis of energy irradiation.

In the embodiment, the method for forming the layer is not specially limited if the method makes the formation of the layer possible. For example, the layer can be formed by applying a coating solution for forming a cell adhesion-inhibiting material layer, which comprises the cell adhesion-inhibiting material by the above-mentioned applying method, or other method.

When concave portions are made in the base material as describe above, it is possible to use: a casting process of forming a photocatalyst-containing layer which will be detailed later onto the concave portions in the base material, dropping down the coating solution for forming a cell adhesion-inhibiting material layer, into the concave portions, and drying so as to form the cell adhesion-inhibiting material layer; an adsorbing process of forming a photocatalyst-containing layer which will be detailed later onto the concave portions in the base material, dropping down the coating solution for forming a cell adhesion-inhibiting material layer, and washing the surface after a given time; or some other process.

The film thickness of the cell adhesion-inhibiting material layer is appropriately selected in accordance with the kind of the cell culture substrate and other factors, and may be usually from about 0.01 to 1.0 μm, preferably from about 0.1 to 0.3 μm.

Specific examples of the cell adhesion-inhibiting material used in the cell adhesion-inhibiting material layer formed in the embodiment may be equivalent to those of the cell adhesion-inhibiting material used in the photocatalyst-containing cell adhesion-inhibiting material layer in the second embodiment. Thus, detailed description thereof is omitted herein. It is preferred that the cell adhesion-inhibiting material layer in the embodiment also comprises the cell adhesive material described about the photocatalyst-containing cell adhesion-inhibiting material layer in the second embodiment. This makes it possible to make the cell adhesive properties of the region irradiated with energy high in the energy irradiating process, which will be detailed later.

In the embodiment also, it is preferred to use, as the cell adhesion-inhibiting material, a material capable of rendering the region irradiated with energy a hydrophilic region and making the cell adhesion-inhibiting portion not irradiated with the energy water repellent in the energy irradiating process which will be detailed later. According to this, at time of applying a cell-containing liquid by a region-selecting applying method in the cell-containing liquid applying process, which will be detailed later, cells do not adhere onto the cell adhesion-inhibiting portion and cells adhere only onto the cell adhesion portion, thereby giving an advantage that the cells can be adhered in a more highly precise pattern form.

Specifically, in the region not irradiated with energy, that is, in the cell adhesion-inhibiting portion having water repellency, the contact angle with water is preferably 100° or more, more preferably from 110 to 130°. If the contact angle with water is smaller than this range, the cell-containing liquid applied by the region-selecting applying method in the cell-containing liquid applying process, which will be detailed later, may adhere onto the cell adhesion-inhibiting portion. In the case of forming irregularities in the base material and measuring the contact angle thereof with water, the contact angle can be made as high as about 160°, as described above.

In the region irradiated with energy, that is, the cell adhesion portion having hydrophilicity, the contact angle with water is preferably 50° or lower, more preferably from 10 to 40°, even more preferably from 15 to 30°. If the contact angle with water is larger than the range, the cell adhesion portion repels the cell-containing liquid applied by the region-selecting applying method in the cell-containing liquid applying process, which will be detailed later, so that cells may not be caused to adhere onto the portion. The contact angle with water referred to herein can be measured by the above-mentioned method.

(5) Fifth Embodiment

The patterning substrate formed according to the fifth embodiment of the present process is a patterning substrate comprising a base material and a cell culture patterning layer which is formed on the base material and has a cell adhesive layer comprising a cell adhesive material that has cell adhesive properties and is decomposed or denatured by action of a photocatalyst on the basis of energy irradiation.

In the embodiment, the cell adhesive layer comprises therein the cell adhesive material, which is decomposed or denatured by action of a photocatalyst on the basis of energy irradiation; therefore, the cell adhesive material in the cell adhesive layer can be decomposed or denatured by energy irradiation by use of a photocatalyst-containing layer side substrate having a base body and a photocatalyst-containing layer comprising the photocatalyst in the energy irradiating process, which will be detailed later. Consequently, a non-cell adhesion portion can be formed. In the embodiment, the cell culture patterning layer does not need to comprise therein any photocatalyst; therefore, a deterioration of the layer with the passage of time can be made small.

The base material used in the embodiment may be the same as described in the first embodiment. The cell adhesive layer may be the same as described in the third embodiment. Thus, detailed description thereof is omitted herein.

(6) Sixth Embodiment

The patterning substrate obtained according to the sixth embodiment of the present process is a patterning substrate comprising a base material and a cell culture patterning layer which is formed on the base material and has a cell adhesion-inhibiting material layer comprising a cell adhesion-inhibiting material that has cell adhesion-inhibiting properties of inhibiting adhesion onto the cells and is decomposed or denatured by action of a photocatalyst on the basis of energy irradiation.

In the embodiment, the cell adhesion-inhibiting material layer comprises therein the cell adhesion-inhibiting material, which is decomposed or denatured by action of a photocatalyst on the basis of energy irradiation; therefore, the cell adhesion-inhibiting material in the cell adhesion-inhibiting material layer can be decomposed or denatured by energy irradiation by use of a photocatalyst-containing layer side substrate having a base body and a photocatalyst-containing layer comprising the photocatalyst in the energy irradiating process, which will be detailed later. In the embodiment, the cell culture patterning layer does not need to comprise therein any photocatalyst; therefore, a deterioration of the layer with the passage of time can be made small.

The base material used in the embodiment may be the same as described in the first embodiment. The cell adhesion-inhibiting material layer may be the same as described in the fourth embodiment. Thus, detailed description thereof is omitted herein.

In the embodiment also, it is preferred to use, as the cell adhesion-inhibiting material, a material capable of rendering the region irradiated with energy a hydrophilic region and making the cell adhesion-inhibiting portion not irradiated with the energy water repellent in the energy irradiating process. According to this, at time of applying a cell-containing liquid by a region-selecting applying method in the cell-containing liquid applying process, which will be detailed later, cells do not adhere onto the cell adhesion-inhibiting portion and cells adhere only onto the cell adhesion portion, thereby giving an advantage that the cells can be adhered in a more highly precise pattern form.

Specifically, in the region not irradiated with energy, that is, in the cell adhesion-inhibiting portion having water repellency, the contact angle with water is preferably 100° or more, more preferably from 110 to 130°. If the contact angle with water is smaller than this range, the cell-containing liquid applied by the region-selecting applying method in the cell-containing liquid applying process, which will be described later, may adhere onto the cell adhesion-inhibiting portion. In the case of forming irregularities in the base material and measuring the contact angle thereof with water, the contact angle can be made as high as about 160°, as described above.

In the region irradiated with energy, that is, the cell adhesion portion having hydrophilicity, the contact angle with water is preferably 50° or lower, more preferably from 10 to 40°, even more preferably from 15 to 30°. If the contact angle with water is larger than the range, the cell adhesion portion repels the cell-containing liquid applied by the region-selecting applying method in the cell-containing liquid applying process, which will be described later, so that cells may not be caused to adhere onto the portion. The contact angle with water referred to herein can be measured by the above-mentioned method.

2. Energy Irradiating Process

The following will describe the energy irradiating process in the method of the invention for producing a cell culture substrate. This energy irradiating process is a process of irradiating energy onto the cell culture patterning layer, thereby forming the cell adhesion portion and the cell adhesion-inhibiting portion in a pattern form by action of a photocatalyst.

The present process can be similarly classified into six embodiments, for irradiating energy and forming the cell adhesion portion and the cell adhesion-inhibiting portion, in accordance with the six embodiments of the patterning substrate.

(1) First Embodiment

The first embodiment of the present process is performed when the patterning substrate is the first embodiment, and is a process of irradiating energy from a given direction, thereby forming a pattern composed of a cell adhesion-inhibiting portion where the cell adhesive material comprised in the photocatalyst-containing cell adhesive layer is decomposed or denatured, and a cell adhesion portion which is other than the cell adhesion-inhibiting portion.

Figure 1B:
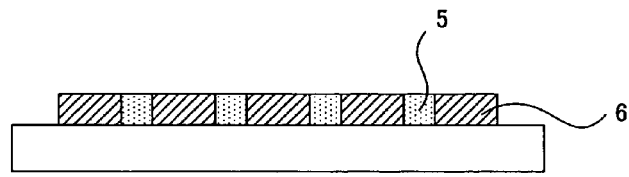

As shown in, for example, FIGS. 1A and 1B, the energy irradiating process of the embodiment is a process of irradiating energy 4 onto a photocatalyst-containing cell adhesive layer 2 which is formed on a base material 1 and comprises the cell adhesive material and a photocatalyst in a pattern form for forming cell adhesion-inhibiting portions through such as a photomask 3 (FIG. 1A). This makes it possible to form cell adhesion-inhibiting portions 5 where the cell adhesive material in the region irradiated with the energy is decomposed or denatured and cell adhesion portions 6 where the cell adhesive material remains without being irradiated with the energy (FIG. 1B).

In the embodiment, energy is irradiated in a pattern form for forming the cell adhesion-inhibiting portion, thereby exciting the photocatalyst comprised in the photocatalyst-containing cell adhesive layer so that the cell adhesive material can be decomposed or denatured. It is therefore possible to render the region irradiated with the energy the cell adhesion-inhibiting portion, where the cell adhesive material is decomposed or denatured, and render the region not irradiated with the energy the cell adhesion portion, where the cell adhesive material remains. At this time, the cell adhesion-inhibiting portion contains the photocatalyst, a decomposition or denaturation product of the cell adhesive material, and so on.

The energy irradiation (exposure) mentioned in the present embodiment is a concept that includes all energy line irradiation that can decompose or denature the cell adhesive material by action of a photocatalyst on the basis of energy irradiation, and is not restricted to light irradiation.

Normally, a wavelength of light used in such energy irradiation is set in the range of 400 nm or less, and preferably in the range of 380 nm or less. This is because, as mentioned above, the photocatalyst that is preferably used as a photocatalyst is titanium dioxide, and as energy that activates a photocatalyst action by the titanium oxide, light having the above-mentioned wavelength is preferable.

As a light source that can be used in such energy irradiation, a mercury lamp, metal halide lamp, xenon lamp, excimer lamp and other various kinds of light sources can be cited.

The method for the exposure may be a method of using a laser, such as an excimer laser or YAG laser, to draw and irradiate energy in a pattern form, besides a method of using a light source as described above to draw and irradiate energy in a pattern form through a photomask. When the base material has light-shielding portions in the same pattern form as the cell adhesion portions have, as described above, the exposure can be performed by irradiating the entire surface of the cell culture patterning substrate from the base material side thereof. These cases have an advantage that a photomask, and positioning and other steps are unnecessary.

When the base material has one or more concave portions and the photocatalyst-containing cell adhesive layers is formed in the concave portion(s), as described above, the exposure may be performed by any one of the above-mentioned methods. For instance, in the case of the plural concave portions, for example, the exposure may be performed into the form of patterns different from each other for the individual concave portions. Examples of the method for performing the exposure into the form of patterns different from each other for the individual concave portions as described above include a method of arranging different masks for the individual concave portions to irradiate energy; and a method of arranging a chromium mask, a stencil mask or the like at the tip of an optical fiber to irradiate energy.

In order not to irradiate any energy onto side walls of the concave portions, the method for the exposure may be, for example, a method of using a cylindrical mask to irradiate energy only onto the bottom faces of the concave portions.

The irradiation quantity of the energy at the time of the energy-irradiation is set to a value necessary for decomposing or denaturing the cell adhesive material by action of the photocatalyst.

It is preferred to irradiate the energy while heating the photocatalyst-containing cell adhesive layer, which comprises a photocatalyst, at this time since the patterning sensitivity can be raised and the cell adhesive material can be effectively decomposed or denatured. Specifically, it is preferred to heat the layer at a temperature of 30 to 80° C.

The energy irradiation through the photomask in the embodiment may be irradiated from either of the side of the base material and the side of the photocatalyst-containing cell adhesive layer when the base material is transparent. On the other hand, when the base material is opaque, the energy needs to be irradiated from the side of the photocatalyst-containing cell adhesive layer.

In the embodiment, it is allowable to cut a part of the patterning substrate where the cell adhesion portion and the cell adhesion-inhibiting portion are formed in a pattern form, which may be referred to as the cell culture patterning substrate hereinafter, stick this part of the cell culture patterning substrate onto such as the bottom of a concave-form base material, and subsequently perform the cell-containing liquid applying process, which will be detailed later.

(2) Second Embodiment

The second embodiment of the present process is performed when the patterning substrate is the second embodiment, and is a process of irradiating energy from a given direction, thereby forming a pattern composed of a cell adhesion portion where the cell adhesion-inhibiting material comprised in the photocatalyst-containing cell adhesion-inhibiting material layer is decomposed or denatured, and a cell adhesion-inhibiting portion which is other than the cell adhesion portion.

In the embodiment, energy is irradiated in a pattern form for forming the cell adhesion portion, thereby exciting the photocatalyst comprised in the photocatalyst-containing cell adhesion-inhibiting material layer so that the cell adhesion-inhibiting material can be decomposed or denatured. It is therefore possible to render the region irradiated with the energy the cell adhesion portion, where the cell adhesion-inhibiting material is decomposed or denatured, and render the region not irradiated with energy the cell adhesion-inhibiting portion, where the cell adhesion-inhibiting material remains. At this time, the cell adhesion portion contains the photocatalyst, a decomposition or denaturation product of the cell adhesion-inhibiting material, and soon. The method for irradiating the energy, and others are the same as in the first embodiment. Thus, description thereof is omitted.

In the embodiment also, it is allowable to cut a part of the patterning substrate where the cell adhesion portion and the cell adhesion-inhibiting portion are formed in a pattern form, which may be referred to as the cell culture patterning substrate hereinafter, stick this part of the cell culture patterning substrate onto such as the bottom of a concave-form base material, and subsequently perform the cell-containing liquid applying process, which will be detailed later.

(3) Third Embodiment

The third embodiment of the present process is performed when the patterning substrate is the third embodiment, and is a process of irradiating energy from a given direction, thereby forming a pattern composed of a cell adhesion-inhibiting portion where the cell adhesive material comprised in the cell adhesive layer is decomposed or denatured, and a cell adhesion portion which is other than the cell adhesion-inhibiting portion.

In the embodiment, energy is irradiated in a pattern form for forming the cell adhesion-inhibiting portion, thereby exciting the photocatalyst in the photocatalyst-containing layer so that the cell adhesive material can be decomposed or denatured. It is therefore possible to render the region irradiated with energy the cell adhesion-inhibiting portion, where the cell adhesive material is decomposed or denatured, and render the region not irradiated with the energy the cell adhesion portion, where the cell adhesive material remains. At this time, the cell adhesion-inhibiting portion comprises a small amount of the cell adhesive material or comprises a decomposition product of the cell adhesive material or the like, or the cell adhesive layer is completely decomposed and removed to make the photocatalyst-containing layer exposed when the cell adhesive material is, for example, a material which can be decomposed by action of the photocatalyst on the basis of energy irradiation. When the cell adhesive material is a material which can be denatured by action of the photocatalyst on the basis of energy irradiation, the cell adhesion-inhibiting portion comprises therein such as a denaturation product thereof. The method for irradiating the energy, and others are the same as in the first embodiment. Thus, description thereof is omitted herein.

In the embodiment also, it is allowable to cut a part of the patterning substrate where the cell adhesion portion and the cell adhesion-inhibiting portion are formed in a pattern form, which may be referred to as the cell culture patterning substrate hereinafter, stick this part of the cell culture patterning substrate onto such as the bottom of a concave-form base material, and subsequently perform the cell-containing liquid applying process, which will be detailed later.

(4) Fourth Embodiment

The fourth embodiment of the present process is performed when the patterning substrate is the fourth embodiment, and is a process of irradiating energy from a given direction, thereby forming a pattern composed of a cell adhesion portion where the cell adhesion-inhibiting material comprised in the cell adhesion-inhibiting material layer is decomposed or denatured and a cell adhesion-inhibiting portion which is other than the cell adhesion portion.

In the embodiment, energy is irradiated in a pattern form for forming the cell adhesion portion, thereby exciting the photocatalyst in the photocatalyst-containing layer so that the cell adhesion-inhibiting material can be decomposed or denatured. It is therefore possible to render the region irradiated with energy the cell adhesion portion, where the cell adhesion-inhibiting material is decomposed or denatured, and render the region not irradiated with the energy, the cell adhesive—inhibiting portion where the cell adhesion-inhibiting material remains.

The wording "the cell adhesion-inhibiting material is decomposed or denatured" means that the cell adhesion-inhibiting material is not comprised, or the cell adhesion-inhibiting material is comprised in a smaller amount than the amount of the cell adhesion-inhibiting material comprised in the cell adhesion-inhibiting portion. When the cell adhesion-inhibiting material is, for example, a material which can be decomposed by action of the photocatalyst on the basis of energy irradiation, the cell adhesion portion comprises a small amount of the cell adhesion-inhibiting material, comprises a decomposition product or the like of the cell adhesion-inhibiting material, the cell adhesion-inhibiting material layer is completely decomposed and removed to make the photocatalyst-containing layer exposed, or the like. When the cell adhesion-inhibiting material is a material which can be denatured by action of the photocatalyst on the basis of energy irradiation, the cell adhesion portion comprises therein such as a denaturation product thereof. In the embodiment, the cell adhesion portion preferably comprises a cell adhesive material having cell adhesive properties at least after the material is irradiated with energy. This makes it possible to make the cell adhesive properties of the cell adhesion portion higher so that cells can be caused to adhere highly precisely only onto the cell adhesion portion. The method for irradiating the energy, and others are the same as in the first embodiment. Thus, description thereof is omitted herein.

In the embodiment also, it is allowable to cut a part of the patterning substrate where the cell adhesion portion and the cell adhesion-inhibiting portion are formed in a pattern form, which may be referred to as the cell culture patterning substrate hereinafter, stick this part of the cell culture patterning substrate onto such as the bottom of a concave-form base material, and subsequently perform the cell-containing liquid applying process, which will be detailed later.

(5) Fifth Embodiment

The fifth embodiment of the present process is performed when the patterning substrate is the fifth embodiment, and is a process of arranging the cell adhesive layer and a photocatalyst-containing layer side substrate having a base body and a photocatalyst-containing layer comprising a photocatalyst to dispose the cell adhesive layer and the photocatalyst-containing layer facing each other, and then irradiating energy onto the resultant from a given direction, thereby forming a pattern composed of a cell adhesion-inhibiting portion where the cell adhesive material comprised in the cell adhesive layer is decomposed or denatured, and a cell adhesion portion which is other than the cell adhesion-inhibiting portion.

Figure 2A:
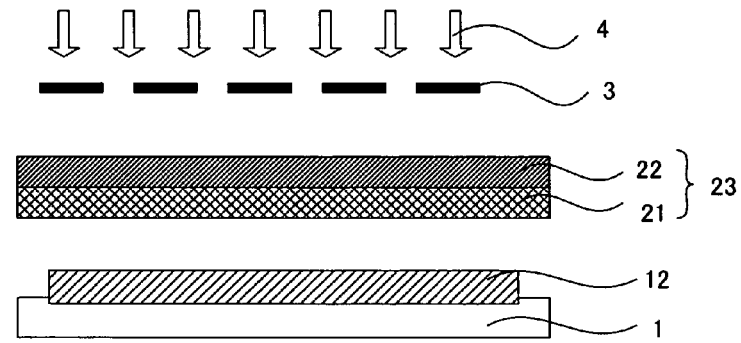
FIGS. 2A and 2B are process charts illustrating another example of the energy irradiating process in the method of the invention for producing a cell culture substrate.
Figure 2B:
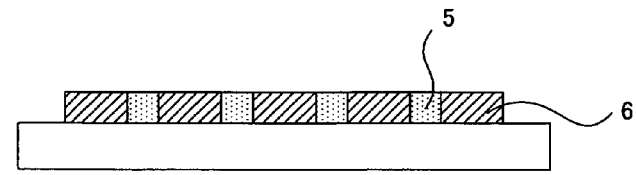

As shown in, for example, FIGS. 2A and 2B, in the energy irradiating process of the embodiment, a cell adhesive layer 12 formed on a base material 1 and a photocatalyst-containing layer side substrate 23, having a photocatalyst-containing layer 21 comprising a photocatalyst and a base body 22, are arranged to dispose the cell adhesive layer 12 and the photocatalyst-containing layer 21 facing each other, and then energy 4 is irradiated, in a pattern form for forming cell adhesion-inhibiting portions, onto the resultant through such as a photomask 3 (FIG. 2A). According to this, regions where the cell adhesive material is decomposed or denatured by the irradiation with the energy are rendered cell adhesion-inhibiting portions 5, and regions where the cell adhesive material remains without being irradiated with the energy are rendered cell adhesion portions 6 (FIG. 2B).

In the embodiment, the photocatalyst-containing layer side substrate is used to irradiate energy in a pattern form for forming the cell adhesion-inhibiting portion, thereby exciting the photocatalyst in the photocatalyst-containing layer so that the cell adhesive material can be decomposed or denatured. It is therefore possible to render the region irradiated with energy the cell adhesion-inhibiting portion, where the cell adhesive material is decomposed or denatured, and render the region not irradiated with the energy the cell adhesion portion, where the cell adhesive material remains. At this time, the cell adhesion-inhibiting portion comprises a small amount of the cell adhesive material or comprises a decomposition product or the like of the cell adhesive material, or the cell adhesive layer is completely decomposed and removed to make the base material exposed when the cell adhesive material is, for example, a material which can be decomposed by action of the photocatalyst on the basis of energy irradiation. When the cell adhesive material is a material which can be denatured by action of the photocatalyst on the basis of energy irradiation, the cell adhesion-inhibiting portion comprises therein such as a denaturation product thereof.

The following will describe the photocatalyst-containing layer side substrate used in the embodiment, which has a photocatalyst-containing layer and a base body, and the method for irradiating the energy.

(a) Photocatalyst-Containing Layer Side Substrate

First, the photocatalyst-containing layer side substrate used in the present embodiment, which has a photocatalyst-containing layer comprising a photocatalyst, is described. The photocatalyst-containing layer side substrate used in the embodiment is normally a substrate having a photocatalyst-containing layer comprising a photocatalyst, and is usually a base body and substrate wherein a photocatalyst-containing layer is formed on the base body. This photocatalyst-containing layer side substrate may have, for example, photocatalyst-containing layer side light-shielding portions formed in a pattern form, a primer layer, or the like. The following will describe each of the constituents of the photocatalyst-containing layer side substrate used in the embodiment.

(i) Photocatalyst-Containing Layer

First, the photocatalyst-containing layer used in the photocatalyst-containing layer side substrate is described. The photocatalyst-containing layer used in the embodiment is not limited to any special structure if the layer has a structure wherein the photocatalyst in the layer can cause the decomposition or denaturation of the cell adhesive material in the adjacent or near cell adhesive layer. The photocatalyst-containing layer may be made of a photocatalyst and a binder, or may be made only of a photocatalyst.

Figure 3:
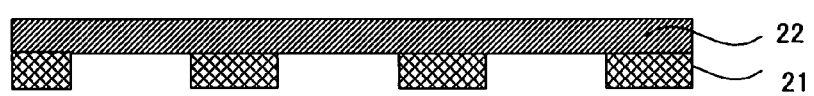
FIG. 3 is a schematic sectional view showing an example of the photocatalyst-containing layer side substrate used in the invention.

The photocatalyst-containing layer used in the embodiment may be the photocatalyst-containing layer 21 as illustrated in, for example, FIG. 2A, which is formed on the whole of a surface of the base body 22; or a photocatalyst-containing layer 21 as illustrated in, for example, FIG. 3, which is formed in a pattern form on a base body 22.

In the case of forming the photocatalyst-containing layer in a pattern form as described above, it is unnecessary that at the time of irradiating energy to form the cell adhesion-inhibiting portion, patterning irradiation using such as a photomask is performed. By full-surface irradiation of the energy at this time, the cell adhesion-inhibiting portion can be rendered a cell adhesion-inhibiting portion where the cell adhesive material comprised in the cell adhesive layer is decomposed or denatured in a pattern form.

The method for patterning the photocatalyst-containing layer is not particularly limited. For example, a method such as a photolithography may be used.

The cell adhesive material only on the cell adhesive layer which actually faces the photocatalyst-containing layer is decomposed or denatured; therefore, the direction in which energy is irradiated may be any direction if the energy is irradiated onto the area where the photocatalyst-containing layer and the cell adhesive layer face each other. There is generated an advantage that the irradiated energy is not particularly limited to energy composed of parallel constituents, such as parallel light rays.

The photocatalyst-containing layer used in the embodiment may be the same as described in the third embodiment in the above-mentioned item "1. Patterning Substrate Forming Process". Thus, detailed description thereof is omitted herein.

(ii) Base Body

The following will describe the base body used in the photocatalyst-containing layer side substrate. The photocatalyst-containing layer side substrate is usually a member having at least the base body and the photocatalyst-containing layer formed on the base body. The material which constitutes the used base body is appropriately selected in accordance with the direction of the energy irradiation which will be detailed later, the matter as to whether or not the pattern-formed body to be obtained needs transparency, and other factors.

The base body used in the present embodiment may be a member having flexibility, such as a resin film, or may be a member having no flexibility, such as a glass plate. This is appropriately selected in accordance with the method for the energy irradiation.

An anchor layer may be formed on the base body in order to improve the adhesive property between the base body surface and the photocatalyst-containing layer. The anchor layer may be made of, for example, a silane-based or titanium-based coupling agent.

(iii) Photocatalyst-Containing Layer Side Light-Shielding Portions

The photocatalyst-containing layer side substrate used in the present embodiment may be a photocatalyst-containing layer side substrate on which photocatalyst-containing layer side light-shielding portions may be formed into a pattern form. When the photocatalyst-containing layer side substrate having photocatalyst-containing layer side light-shielding portions is used in this way, it is unnecessary to use, at the time of irradiating energy, any photomask or to irradiate a laser ray for drawing irradiation. It is therefore unnecessary to position a photomask precisely onto the photocatalyst-containing layer side substrate. Consequently, it is unnecessary to use any complicated step or any expensive device for drawing irradiation, thereby producing an advantage for costs.

Such a photocatalyst-containing layer side substrate having photocatalyst-containing layer side light-shielding portions can be classified into the following two embodiments, depending on the position where the photocatalyst-containing layer light-shielding portions are formed.

Figure 4:
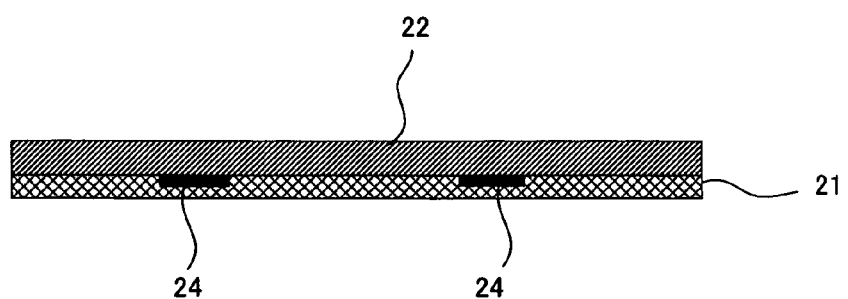
FIG. 4 is a schematic sectional view showing another example of the photocatalyst-containing layer side substrate used in the invention.

One of them is an embodiment as illustrated in, for example, FIG. 4, wherein photocatalyst-containing layer side light-shielding portions 24 are formed on a base body 22 and further a photocatalyst-containing layer 21 is formed on the photocatalyst-containing layer side light-shielding portions 24, thereby preparing a photocatalyst-containing layer side substrate. The other is an embodiment as illustrated in, for example, FIG. 5, wherein a photocatalyst-containing layer 21 is formed on a base body 22 and further photocatalyst-containing layer side light-shielding portions 24 are formed thereon, thereby preparing a photocatalyst-containing layer side substrate.

In any one of the embodiments, the effect of energy-scattering in the base body or the like can be made smaller than in the case of using a photomask since the photocatalyst-containing layer side light-shielding portions are arranged near the region where the photocatalyst-containing layer and the cell adhesive layer are arranged. Accordingly, irradiation of energy in a pattern form can be extremely precisely attained.

Figure 5:
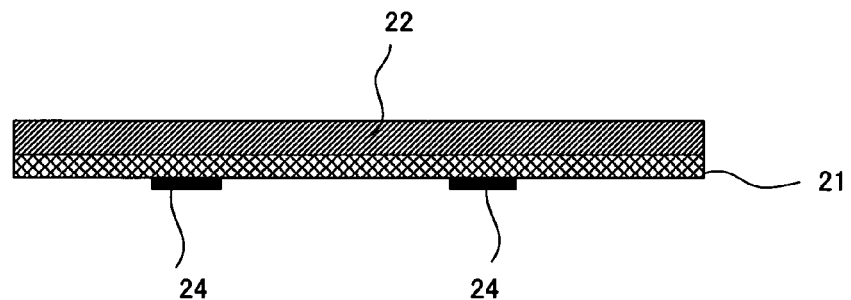
FIG. 5 is a schematic sectional view showing still another example of the photocatalyst-containing layer side substrate used in the invention.

In the present embodiment, an embodiment wherein photocatalyst-containing layer side light-shielding portions 24 are formed on a photocatalyst-containing layer 21 as shown in FIG. 5 has an advantage that at the time of arranging the photocatalyst-containing layer and the cell adhesive layer in a predetermined position, the film thickness of the light-shielding portions can be made consistent with the width of the interval between the two layers, thereby using the light-shielding portions as a spacer for making the interval constant.

In other words, when the photocatalyst-containing layer and the cell adhesive material layer are arranged so as to be facing each other at a given interval, the photocatalyst-containing layer side light-shielding portions and the cell adhesive layer can be made closely adhesive to each other, thereby making the dimension of the given interval precise. When the resultant in this state is irradiated with energy, cell adhesion-inhibiting portions can be formed with a good precision since no cell adhesive material is decomposed or denatured in the cell adhesive layer inside the region where the cell adhesive layer and the light-shielding portions contact.

The method for forming the photocatalyst-containing layer side light-shielding portions is not specially limited, and is appropriately selected in accordance with properties of the face where the photocatalyst-containing layer side light-shielding portions are to be formed, the performance of shielding required energy, and other factors. The method may be the same method for forming the light-shielding portions, which are formed on the base material, described about the first embodiment in the item "1. Patterning Substrate Forming Process". Thus, detailed description is omitted herein.

The above has described two cases, wherein the photocatalyst-containing layer side light-shielding portions are formed between the base body and the photocatalyst-containing layer and are formed on the surface of the photo catalyst-containing layer. Besides, the photocatalyst-containing layer side light-shielding portions may be formed on the base body surface on which no photocatalyst-containing layer is formed. In this embodiment, for example, a photomask can be made close to this surface to such a degree that the photomask can be put on and taken off. Thus, this embodiment can be preferably used for the case that the pattern of the cell adhesion-inhibiting portions is varied for every small lot.

(iv) Primer Layer

The following will describe a primer layer used in the photocatalyst-containing layer side substrate of the embodiment. When photocatalyst-containing layer side light-shielding portions are formed into a pattern form on a base body and a photocatalyst-containing layer is formed thereon so as to prepare a photocatalyst-containing layer side substrate described above, a primer layer may be formed between the photocatalyst-containing layer side light-shielding portions and the photocatalyst-containing layer.

The effect and function of this primer layer are not necessarily clear, but would be as follows: the primer layer is formed between the photocatalyst-containing layer side light-shielding portions and the photocatalyst-containing layer, whereby the primer layer exhibits a function of preventing the diffusion of impurities from openings which are present in and between the light-shielding portions, the impurities being factors for blocking the decomposition or denaturation of the cell adhesive material by action of the photocatalyst, in particular, residues generated when the photocatalyst-containing layer side light-shielding portions are patterned, or metal or metal ion impurities. Accordingly, the formation of the primer layer makes it possible that the processing of the decomposition or denaturation of the cell adhesive material advances with high sensitivity so as to yield cell adhesion-inhibiting portions which are highly precisely formed.

The primer layer in the present embodiment is a layer for preventing the effect of the photocatalyst from being affected by the impurities present inside not only the photocatalyst-containing layer side light-shielding portions but also the openings made between the light-shielding portions. It is therefore preferred to form the primer layer over the entire surface of the light-shielding portions plus the openings.

The primer layer in the present embodiment is not limited to any special structure if the primer layer is formed not to bring the photocatalyst-containing layer side light-shielding portions and the photocatalyst-containing layer of the photocatalyst-containing layer side substrate into contact with each other.

A material that forms the primer layer, though not particularly restricted, is preferably an inorganic material that is not likely to be decomposed by action of the photocatalyst. Specifically, amorphous silica can be cited. When such amorphous silica is used, a precursor of the amorphous silica is preferably a silicon compound that is represented by a general formula, $SiX_4$, X being halogen, methoxy group, ethoxy group, acetyl group or the like, silanol that is a hydrolysate thereof, or polysiloxane having an average molecular weight of 3000 or less.

A film thickness of the primer layer is preferably in the range of 0.001 to 1 µm and particularly preferably in the range of 0.001 to 0.1 µm.

b. Energy Irradiating Method

The following will describe the energy irradiating method in the present embodiment. In the embodiment, the cell adhesive layer and the photocatalyst-containing layer of the photocatalyst-containing layer side substrate are arranged at a given interval, and energy is irradiated onto the resultant.

The above-mentioned wording "arranging" means that the above-mentioned two layers; the photocatalyst-containing layer and the cell adhesive layer are arranged in the state that the action of the photocatalyst can substantially work to the surface of the cell adhesive layer, and include not only the state that the two layers actually contact each other, but also the state that the two layers are arranged at a given interval. The dimension of the interval is preferably 200 µm or less.

The dimension of the above-mentioned interval in the embodiment is more preferably from 0.2 to 10 µm, even more preferably from 1 to 5 µm since the precision of the pattern to be obtained becomes very good and further the sensitivity of the photocatalyst becomes high so as to make good the efficiency of the decomposition or denaturation of the cell adhesive material in the cell adhesive layer. This range of the interval dimension is particularly effective for the cell adhesive layer small in area, which makes it possible to control the interval dimension with a high precision.

Meanwhile, in the case of treating the cell adhesive layer large in area, for example, 300 mm or more×300 mm or more in size, it is very difficult to make a fine interval as described above between the photocatalyst-containing layer side substrate and the cell adhesive layer without contacting each other. Accordingly, when the cell adhesive layer has a relatively large area, the interval dimension is preferably from 10 to 100 µm, more preferably from 50 to 75 µm. The limitation of the interval dimension into this range gives an advantageous effect that the cell adhesive material is not unevenly decomposed or denatured without causing problems based on a fall in patterning precision, such as a problem that a blurred pattern is obtained, or other problems, such as a problem that the sensitivity of the photocatalyst deteriorates so that the efficiency of decomposing or denaturing the cell adhesive material also deteriorates.

When energy is irradiated onto the cell adhesive material having a relatively large area as described above from an energy irradiating device, a unit for positioning the photocatalyst-containing layer side substrate and the cell adhesive layer inside the device is permitted to set the dimension of the interval therebetween preferably into the range of 10 to 200 µm, more preferably into the range of 25 to 75 µm. The setting of the interval dimension value into this range makes it possible to arrange the photocatalyst-containing layer side substrate and the cell adhesive layer without causing a large drop in patterning precision or in sensitivity of the photocatalyst, or bringing the substrate and the layer into contact with each other.

When the photocatalyst-containing layer and the surface of the cell adhesive layer are arranged at a given interval as described above, active oxygen species generated from oxygen and water by action of the photocatalyst can easily be released. In other words, if the interval between the photocatalyst-containing layer and the cell adhesive layer is made narrower than the above-mentioned range, the active oxygen species are not easily released, so as to make the rate for decomposing or denaturing the cell adhesive material unfavorably small. If the two layers are arranged at an interval larger than the above-mentioned range, the generated active oxygen species do not reach the cell adhesive layer easily. In this case also, the rate for decomposing or denaturing the cell adhesive material becomes unfavorably small.

The method for arranging the photocatalyst-containing layer and the cell adhesive layer to make such a very small interval evenly therebetween is, for example, a method of using spacers. The use of the spacers in this way makes it possible to make an even interval. In regions which the spacers contact, the action of the photocatalyst does not work onto the surface of the cell adhesive layer; therefore, when the spacers are rendered spacers having a pattern similar to that of the cell adhesion portions, the cell adhesive material only inside regions where no spacers are formed can be decomposed or denatured so that highly precise cell adhesion-inhibiting portions can be formed. The use of the spacers also makes it possible that the active oxygen species generated by action of the photocatalyst reach the surface of the cell adhesive layer, without diffusing, at a high concentration. Accordingly, highly precise cell adhesion-inhibiting portions can be effectively formed.

When the base material has one or more concave portions and the cell adhesive layer is formed in the concave portion(s) as described above, energy may be irradiated onto the entire surface thereof by the above-mentioned method. In the case of the plural concave portions, for example, the exposure may be performed into the form of patterns different from each other for the individual concave portions. Examples of the method for performing the exposure into the form of patterns different from each other for the individual concave portions as described above include a method of arranging different masks for the individual concave portions to irradiate energy by use of the above-mentioned photocatalyst-containing layer side substrate; and a method of arranging the photocatalyst-containing layer side substrate and a chromium mask, a stencil mask or the like at the tip of an optical fiber to irradiate energy.

In order not to radiate any energy onto side walls of the concave portions, the method for the exposure may be, for example, a method of using a cylindrical mask to irradiate energy only onto the bottom faces of the concave portions.

In the embodiment, it is sufficient that such arrangement state of the photocatalyst-containing layer side substrate is maintained only during the irradiation of energy.

The energy irradiation (exposure) mentioned in the present embodiment is a concept that includes all energy line irradiation that can decompose or denature the cell adhesive material by action of a photocatalyst on the basis of energy irradiation, and is not restricted to light irradiation.

The kind of the energy irradiated in the embodiment and related matters thereof may be the same as described in the first embodiment. Thus, detailed description thereof is omitted.

The energy through the photomask in the embodiment may be irradiated from either of the side of the base material and the side of the photocatalyst-containing layer side substrate when the base material is transparent. On the other hand, when the base material is opaque, the energy needs to be irradiated from the side of the photocatalyst-containing layer side substrate.

In the embodiment also, it is allowable to cut a part of the patterning substrate where the cell adhesion portion and the cell adhesion-inhibiting portion are formed in a pattern form, which may be referred to as the cell culture patterning substrate hereinafter, stick this part of the cell culture patterning substrate onto such as the bottom of a concave-form base material, and subsequently perform the cell-containing liquid applying process, which will be detailed later.

(6) Sixth Embodiment

The sixth embodiment of the present process is performed when the patterning substrate is the sixth embodiment, and is a process of arranging the cell adhesion-inhibiting material layer and a photocatalyst-containing layer side substrate having a base body and a photocatalyst-containing layer comprising a photocatalyst to dispose the cell adhesion-inhibiting material layer and the photocatalyst-containing layer facing each other, and then irradiating energy onto the resultant from a given direction, thereby forming a pattern composed of a cell adhesion portion where the cell adhesion-inhibiting material comprised in the cell adhesion-inhibiting material layer is decomposed or denatured, and a cell adhesion-inhibiting portion which is other than the cell adhesion portion.

In the embodiment, the photocatalyst-containing layer side substrate is used to irradiate energy in a pattern form for forming the cell adhesion portion, thereby exciting the photocatalyst in the photocatalyst-containing layer so that the cell adhesion-inhibiting material can be decomposed or denatured. It is therefore possible to render the region irradiated with energy the cell adhesion portion, where the cell adhesion-inhibiting material is decomposed or denatured, and render the region not irradiated with the energy the cell adhesive—inhibiting portion, where the cell adhesion-inhibiting material remains.

The wording "the cell adhesion-inhibiting material is decomposed or denatured" means that the cell adhesion-inhibiting material is not comprised, or the cell adhesion-inhibiting material is comprised in a smaller amount than the amount of the cell adhesion-inhibiting material comprised in the cell adhesion-inhibiting portion. When the cell adhesion-inhibiting material is, for example, a material which can be decomposed by action of the photocatalyst on the basis of energy irradiation, the cell adhesion portion comprises a small amount of the cell adhesion-inhibiting material or comprises a decomposition product of the cell adhesion-inhibiting material, the cell adhesion-inhibiting material layer is completely decomposed and removed to make the base material exposed, or the like. When the cell adhesion-inhibiting material is a material which can be denatured by action of the photocatalyst on the basis of energy irradiation, the cell adhesion portion comprises therein such as a denaturation product thereof. In the embodiment, the cell adhesion portion preferably comprises a cell adhesive material having cell adhesive properties at least after the material is irradiated with energy. This makes it possible to make the cell adhesive properties of the cell adhesion portion higher so that cells are caused to adhere highly precisely only onto the cell adhesion portion. The method for irradiating the energy, and others are the same as in the fifth embodiment. Thus, description thereof is omitted herein.

In the embodiment also, it is allowable to cut a part of the patterning substrate where the cell adhesion portion and the cell adhesion-inhibiting portion are formed in a pattern form, which may be referred to as the cell culture patterning substrate hereinafter, stick this part of the cell culture patterning substrate onto such as the bottom of a concave-form base material, and subsequently perform the cell-containing liquid applying process, which will be detailed later.

3. Cell-Containing Liquid Applying Process

Lastly, the cell-containing liquid applying process in the method of the invention for producing a cell culture substrate will be described. The cell-containing liquid applying process is a process of applying a cell-containing liquid onto the cell adhesion portion by a region-selecting applying method of applying the cell-containing liquid selectively onto the patterned cell adhesion portion.

As described above, a cell-containing liquid is applied by the region-selecting applying method in the invention; therefore, the resultant cell culture substrate can be rendered a highly precise cell culture substrate and further two or more kinds of cells can also be caused to adhere onto the substrate.

The following will describe each of the method and the elements in the present process.

(Region-Selecting Applying Method)

The region-selecting applying method in the invention is a method capable of causing a liquid to adhere selectively only onto one or more given regions. Examples of the method include jetting-out methods such as ink-jetting method, printing methods such as letterpress printing, intaglio printing and gravure printing, and a pen point adhesion method of absorbing a liquid into a convex tip by use of such as a capillary phenomenon and bringing this tip into contact with a substrate to cause the liquid to adhere onto the substrate.

In the invention, it is preferred to use a jetting-out method such as ink-jetting method. When this jetting-out method is used to apply a cell-containing liquid onto the cell adhesion portion, a relatively large amount of the cell-containing liquid can be caused to adhere onto the cell adhesion portion. In the invention, the use of ink-jetting method is more preferred. The use of the ink-jetting method makes it possible to cause the cell-containing liquid to adhere very precisely and effectively onto the cell adhesion portion. It is also possible to arrange plural kinds of cells in arbitrary positions by using plural cell-containing liquids containing different kinds of cells and plural ink-jetting devices.

The ink-jetting method used in the invention may be any ink-jetting method that does not give damage to cells, and may be an ink-jetting method using any one selected from various manners such as a manner of electrifying a cell-containing liquid and jetting out this liquid while controlling the liquid by a magnetic field, a manner of using a piezoelectric element to jet out an ink intermittently, a manner of heating an ink and using bubbles therefrom to jet out the ink intermittently, an electrostatic jetting manner, an ultrasonic jetting manner, a centrifugal jetting manner, and an inertia force head manner. In the invention, it is particularly preferred to use ink-jetting using a piezoelectric element. Since the piezoelectric element using method does not require the cell-containing liquid to be heated or other processes, the method is preferred as a method for causing living cells to adhere onto a substrate.

In the invention, it is preferred that the application of the cell-containing liquid by the region-selecting applying method is performed in an atmosphere having a temperature or humidity at which cells are not dried or annihilated. The atmosphere is appropriately selected in accordance with the kind of the cell-containing liquid which will be detailed later, and other factors. Usually, the temperature is preferably from about 20 to 40° C., and the humidity is preferably from about 80 to 100%. In such an environment, microorganisms besides target cells breed easily. It is therefore preferred to perform the application in a sterilized environment and give a sterilizing function to a device used in the region-selecting applying method.

(Cell-Containing Liquid)

The cell-containing liquid used in the embodiment is not limited to any special kind if the liquid is a liquid which contains cells that can be caused to adhere onto the cell adhesion portion and cultured and which is stable when the liquid is applied by the region-selecting applying method. The cell-containing liquid is appropriately selected in accordance with the kind of the region-selecting applying method and other factors.

the cell—containing liquid may contain, for example, a culture solution, or a biological cell adhesive material besides cells. To protect the cells, the cells may be micro-encapsulated.

As a cell used in the present invention, except for, for instance, non-adhesive cells such as nervous tissue, liver, kidney, pancreas, blood vessel, brain, cartilage and blood corpuscle, all tissues present in an organism and cells derived therefrom can be used. Furthermore, since even for generally non-adhesive cells, recently, in order to adhere and fix, a technology of modifying a cell membrane is devised; accordingly, as needs arise, the non-adhesive cells, when this technology is applied, can be used in the present invention.

The respective tissues such as mentioned above are formed of cells having various functions; accordingly, it is necessary to select desired cells to use. For instance, in the case of the liver, it is formed of, other than hepatocytes, epithelial cells, endothelial cells, Kupffer's cells, fibroblasts, and fat-storing cells and the like. In this case, since the adhesiveness with a cell adhesive portion is different depending on the kinds of the cells, in accordance with a cell strain, a cell adhesive material used in the cell adhesion portion and a composition ratio thereof or the like have to be selected.

The cell-containing liquid used in the cell-containing liquid applying process of the invention may be the same as described in the item "Ink-Jetting Cell-Containing Liquid". Thus, detailed description is omitted herein.

It is preferred that the cell—containing liquid is kept at a constant temperature when the liquid is applied by the region-selecting applying method or in the device for the method. This is because cells are easily affected by temperature and are annihilated outside a given temperature range.

(Cell Adhesion Portion)

The following will describe the cell adhesion portion onto which the cell-containing liquid is applied in the present process. In the invention, the cell adhesion portion and the cell adhesion-inhibiting portion are formed in a pattern form in the above-mentioned energy irradiating process. It therefore becomes possible in the present process to apply the cell-containing liquid only onto the cell adhesion portion without causing the cell-containing liquid to adhere onto the cell adhesion-inhibiting portion.

In the present process, the cell adhesion portion, which is irradiated with energy in the energy irradiating process, can be made hydrophilic and the cell adhesion-inhibiting portion can be made water repellent, in particular, in the case of the second, fourth and sixth embodiments described about the above-mentioned patterning substrate forming process. Accordingly, when the cell-containing liquid is applied, the cell-containing liquid does not adhere onto the cell adhesion-inhibiting portion so that cells can be caused to adhere more highly precisely only onto the cell adhesion portion. According to a report, when cells are caused to adhere onto the boundary region between property-different regions of hydrophilic and water repellent regions, a form-change, such as extension or orientation, is caused in accordance with the kind of the cells. Accordingly, in the above-mentioned embodiments, the form of the cells caused to adhere onto the cell adhesion portion is changed as the case may be, so that the organization of the cells can be promoted.

It is preferred to keep the cell adhesion portion at a given temperature when the cell-containing liquid is applied. This is based on the following reason: in this case also, cells are easily affected by temperature; therefore, the cells applied onto the cell adhesion portion are annihilated outside a given temperature range.

4. Others

If necessary, the method of the invention for producing a cell culture substrate may comprise a process other than the above-mentioned processes. Examples of the process include a pattern maintaining process of using the action of the photocatalyst to maintain the pattern.

In the case of the first, third and fifth embodiments described about the above-mentioned pattern, the pattern maintaining process is a process of causing the cell-containing liquid onto the cell adhesion portion and then giving the action of the photocatalyst on the basis of energy irradiation to the cell adhesion-inhibiting portion, whereby the cells adhering onto the cell adhesion-inhibiting portion can be removed so that the pattern adhering onto the cell adhesion portion can be highly precisely maintained.

In the first and third embodiments, the pattern maintaining process can be performed, for example, by irradiating energy onto the patterning substrate through a photomask having openings in the form of the pattern of the above-mentioned cell adhesion-inhibiting portion(s). In the fifth embodiment, the pattern maintaining process can be performed by disposing the cell adhesive layer and the photocatalyst-containing layer side substrate to face to each other and then irradiating energy onto the patterning substrate through such as a photomask having openings in the form of the pattern of the cell adhesion-inhibiting portion(s).

When the base material is transparent and one or more light-shielding portions are formed in the form of the pattern of the above-mentioned cell adhesion portion(s) in any one of the above-mentioned embodiments, the pattern maintaining process can be performed by irradiating energy onto the patterning substrate from the base material side thereof without using any photomask.

No special limitation is imposed to the energy irradiated at this time if the energy is energy capable of removing the cells adhering onto the cell adhesion-inhibiting portion(s) by action of the photocatalyst on the basis of the energy irradiation. The energy may be the same as irradiated in the above-mentioned energy irradiating process.

The pattern maintaining process may be performed immediately after the cell-containing liquid applying process of applying the cell-containing liquid on the cell adhesion portion(s). When the cells on the cell adhesion portion(s) are cultured for a given period, the pattern maintaining process may be performed at an appropriate time in accordance with the kind or the state of the cells in order not to cause such an inconvenience that the cells adhere onto the cell adhesion-inhibiting portion to make the pattern thick. The pattern maintaining process may be repeated.

B. Ink-Jetting Cell-Containing Liquid

The following will describe the ink-jetting cell-containing liquid (i.e., the cell-containing liquid for ink-jet). The cell-containing liquid can be classified into two embodiments. Each of the embodiments will be described hereinafter.

1. First Embodiment

The first embodiment of the ink-jetting cell-containing liquid of the invention is an ink-jetting cell-containing liquid which comprises cells, a culture solution and a biological cell adhesive material, and which is jet out in a pattern form onto a substrate by ink-jetting method, thereby forming a cell culture substrate onto which the cells adhere in the pattern form.

In the embodiment, the ink-jetting cell-containing liquid comprises therein the biological cell adhesive material; therefore, the adhesive property between the cells jetted-out on the substrate and the substrate can be made good.

It is preferred to use the ink-jetting cell-containing liquid used in the embodiment in, for example, the above-mentioned method for producing a cell culture substrate. This makes it possible such as that when the cells are cultured after the adhesion of the cells, the cells are regularly arranged or undergo a form-change so as to form tissues.

The following will describe each of the materials of the ink-jetting cell-containing liquid.

(Cells)

First, the cells used in the embodiment are described. The cells are not limited to any special kind if the cells can be jetted out by ink-jetting method and further the cells are stable when and after the cells are jetted.

The size of the cells that can be jetted out by ink-jetting method is usually from about 1 to 50 μm, preferably from about 10 to 20 μm. Examples of the cells having such a size include hepatocytes, Langerhans' islet cells, and vascular endothelial cells.

The content of such cells is appropriately selected in accordance with the kind of the cells, the pore size of an ink-jetting device, or other factors. Usually, the content is preferably from $1 \times 10^5$ to $1 \times 10^{10}$ cells/ml of the cell-containing liquid of the embodiment, more preferably from $1 \times 10^6$ to $1 \times 10^8$ cells/ml thereof.

(Culture Solution)

The following will describe the culture solution used in the embodiment. The culture solution is a solution for culturing cells mentioned above. The above-mentioned cells can be stably present in an ink-jetting device or the like without being annihilated or the like.

The material used in this culture solution is preferably a material which is stable after it is jetted out from an ink-jetting device. Examples thereof include mixtures of amino acids, vitamins, sugars, and salt. In the embodiment, it is preferred to use a solution wherein the biological cell adhesive material which will be detailed later or a serum is added to an Eagle's basal medium, a Fisher's medium or a ham's medium, in which necessary amounts of the above-mentioned components are mixed beforehand, or an improved product thereof.

The content by percentage of the culture solution in the cell-containing liquid of the embodiment is appropriately selected in accordance with the kind of the cells, or other factors. Usually, the content is preferably from 0.5 to 2.0% by weight, more preferably from 1.0 to 1.5% by weight.

(Biological Cell Adhesive Material)

The following will describe the biological cell adhesive material used in the embodiment. The biological cell adhesive material is a material by which at the time of applying the ink-jetting cell-containing liquid of the embodiment onto a substrate or the like, the adhesive property between the cells and the base material is made good.

The biological cell adhesive material is, for example, a material good in adhesive properties to a specific kind of cells, or a material good in adhesive properties to many kinds of cells. Specific examples thereof include fibronection, laminin, tenascin, vitronection, RGD (alginine-glycine-asparagic acid) sequence containing peptide, YIGSR (tyrosine-isoleucine-glycine-serine-arginine) sequence containing peptide, collagen, atelocollagen, and gelatin. Of these, atelocollagen and gelatin are preferred from the viewpoint of the adjustment of the concentration and viscosity of the cell-containing liquid.

Usually, the content by percentage of the biological cell adhesive material in the cell-containing liquid of the embodiment is appropriately selected in accordance with the kind of the cells, the kind of the biological cell adhesive material, and other factors, and is preferably from 0.01 to 5.0% by weight, more preferably from 0.5 to 2.0% by weight.

2. Second Embodiment

The following will describe the second embodiment of the ink-jetting cell-containing liquid of the present invention. The ink-jetting cell-containing liquid of the embodiment is an ink-jetting cell-containing liquid which is jet out in a pattern form onto a substrate by ink-jetting method, thereby forming a cell culture substrate onto which cells adhere in the pattern form, the cells being micro-encapsulated.

Since the used cells are micro-encapsulated in the embodiment, the cells themselves are not damaged when jetted out by ink-jetting method so that the survival rate of the jetted-out cells can be improved. It is therefore to improve the yield of the cell culture substrates obtained by use of the ink-jetting cell-containing liquid.

It is preferred to use the ink-jetting cell-containing liquid used in the embodiment in, for example, the above-mentioned method for producing a cell culture substrate. This makes it possible such as that when the cells are cultured after the adhesion of the cells, the cells are regularly arranged or undergo a form-change so as to form tissues.

The following will describe each of the materials of the ink-jetting cell-containing liquid.

(Cells)

The cells used in the embodiment are cells contained in the microcapsules which will be detailed later. The cells are not limited to any special kind if the cells are stable in the microcapsules and are further stable when and after the cells are jetted from an ink-jetting device.

Examples of the cells include hepatocytes, Langerhans' islet cells, vascular endothelial cells, and cells which are poor in adhesive property to a substrate and are easily damaged, such as brain cells and nerve cells.

The number of the cells contained in the microcapsules, which will be detailed below, is usually from 1 to 100.

(Microcapsules)

The following will describe the microcapsules used in the embodiment. No special limitation is imposed on the microcapsules if the microcapsules contain the above-mentioned cells and protect the cells from impact, heat or the like when jetted out from an ink-jetting device. The microcapsules are, for example, microcapsules wherein the cell-containing liquid is contained in a capsule membrane made of a gel compound such as gelatin. Such capsules can be formed, for example, by dropping down the material of the membrane and the cell-containing liquid from concentric nozzles. In general, such microcapsules have a diameter of about 100 µm to several millimeters, but the microcapsules in the present manner desirably have a diameter of about 100 to 300 µm.

C. Ink-Jetting Device for Producing a Cell Culture Substrate

Lastly, the ink-jetting device of the invention for producing a cell culture substrate is described. The ink-jetting device is an ink-jetting device for producing a cell culture substrate comprising a cell-containing liquid supplying section into which a cell-containing liquid is filled, a jetting-out section having a piezoelectrically driving head unit for jetting out the cell-containing liquid supplied from the cell-containing liquid supplying section onto a cell culture patterning substrate, and a stage for fixing the cell culture patterning substrate, wherein the cell-containing liquid supplying section is provided with a stirring means for dispersing cells homogeneously in the filled cell-containing liquid, and the jetting-out section and stage are provided with one or more temperature controlling means for keeping the temperature of the cell-containing liquid constant before and after the jetting-out.

In the invention, the stirring means is arranged in the cell-containing liquid supplying section; therefore, cells can be made into the state that the cells are homogeneously dispersed in the cell-containing liquid inside the supplying section. Accordingly, the content by percentage of the cells in the jetted-out cell-containing liquid can be made constant so that the number of the cells adhering onto the resultant cell culture substrate can be made even. This makes it possible to render the cell culture substrate a high-quality cell culture substrate. In the invention, the ink-jetting device has the temperature controlling means for keeping the temperature of the jetting-out section and the stage constant; therefore, it is possible to prevent the annihilation of the cells, for example, in the cell-containing liquid in the cell-containing liquid supplying section and in a channel extending from this cell-containing liquid supplying section to orifices of the piezoelectrically driving head unit, and in the cell-containing liquid jetted-out onto the cell culture patterning substrate fixed onto the stage, thereby improving the survival rate of the cells. Thus, the yield of the resultant cell culture substrates can be improved.

Figure 6:
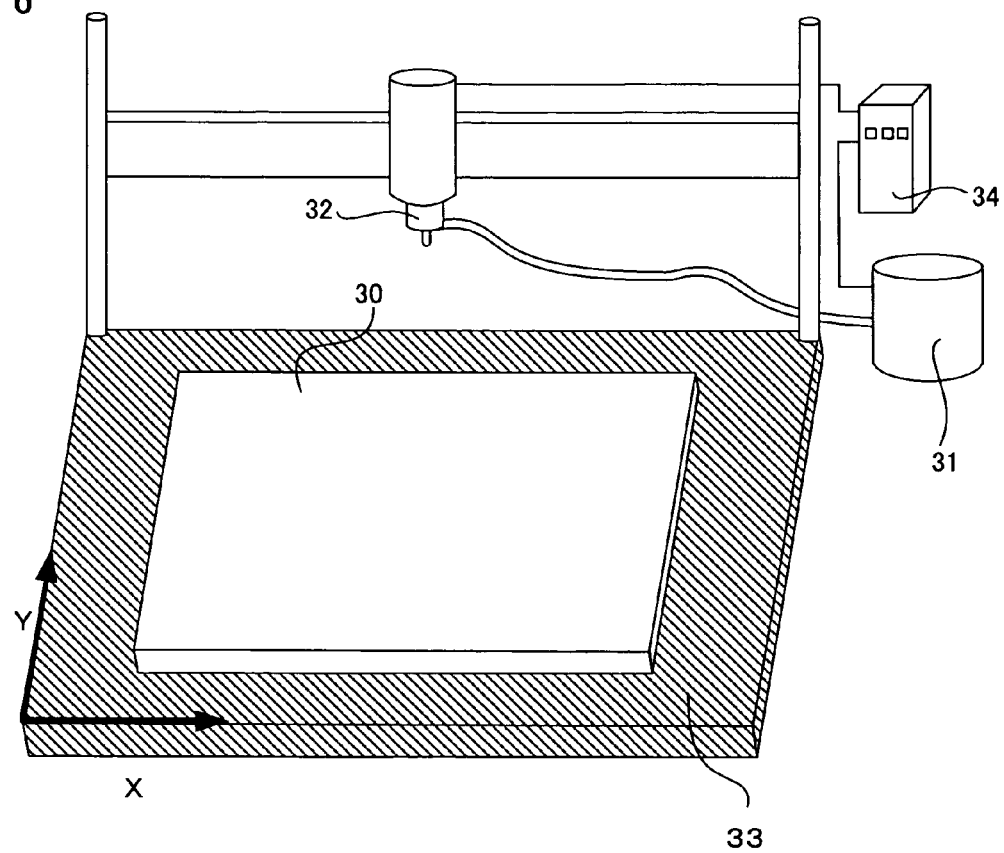
FIG. 6 is a schematic sectional view illustrating an ink-jetting device for producing a cell culture substrate of the invention.

As shown in, for example, FIG. 6, in an ink-jetting device of the invention for producing a cell culture substrate, a cell-containing liquid is filled into a cell-containing liquid supplying section and this cell-containing liquid supplying section 31 is provided with a stirring means. The device also has a piezoelectrically driving head unit for jetting out the cell-containing liquid supplied from this cell-containing liquid supplying section 31 onto a target cell culture patterning substrate 30, and further has a jetting-out section 32 having a temperature controlling means. Furthermore, a stage 33 onto which the cell culture patterning substrate 30 will be fixed is also provided with a temperature controlling means. In order to apply the cell-containing liquid onto a target location therein at this time, the stage 33 may be moved or the jetting-out section 32 may be moved. Both of them may be moved.

The device may be provided with such as a control section 34 for controlling stirring in the cell-containing liquid supplying section 31 and the temperature of the section 31 and controlling the temperature of the jetting-out section 32.

The cell-containing liquid used in the ink-jetting device of the invention for producing a cell culture substrate is not limited to any special kind if the liquid is stable when jetted out or stored in the cell-containing liquid supplying section. It is particularly preferred to use the cell-containing liquid described in the item "B. Ink-Jetting Cell-Containing Liquid". This makes it possible to jet out cells stably and improve the yield of the resultant cell culture substrates. The cell culture patterning substrate onto which the cell-containing liquid will be jetted is not limited to any special kind if the substrate is a substrate capable of culturing the jetted-out cells. In the invention, the substrate is in particular preferably a substrate having a cell culture patterning layer having a cell adhesion portion and a cell adhesion-inhibiting portion as described in the item "A. Method for Producing a Cell Culture Substrate". This makes it possible to arrange the jetted-out cells along a pattern of the cell adhesion portion and the cell adhesion-inhibiting portion or change the form of the cells so as to culture the cells into a tissue easily. It is preferred that on the cell culture patterning substrate a position-detecting mark is formed at a given location therein. This makes the positioning of the cell culture patterning substrate easy, whereby the cell-containing liquid can be very precisely applied selectively only onto the cell adhesion portion. No special limitation is imposed on the position-detecting mark if the mark can be detected. Thus, the mark may be such as the same mark as is ordinarily used for the positioning of substrates.

The following will describe each of the constituents of the ink-jetting device of the invention for producing a cell culture substrate.

1. Cell-Containing Liquid Supplying Section

First, the cell-containing liquid supplying section of the ink-jetting device of the invention for producing a cell culture substrate is described. The cell-containing liquid supplying section of the ink-jetting device of the invention for producing a cell culture substrate is not limited to any special structure if the section is a section which can be filled with the cell-containing liquid and has a function of stirring the cell-containing liquid.

The above-mentioned stirring function is any function that makes it possible to disperse the filled cell-containing liquid homogeneously, without giving any damage resulting from the stirring to the cells in the cell-containing liquid or lowering the activity of the cells, in order to prevent the cells from being precipitated or annihilated in the cell-containing liquid. This function can be fulfilled by, for example, rotary stirring or vibratory stirring.

It is preferred that the cell-containing liquid supplying section is kept at a constant temperature. The temperature thereof may be adjusted with a temperature adjusting means of the jetting-out section which will be detailed below, or may be adjusted with a temperature adjusting means set separately to the present section.

2. Jetting-Out Section

The following will describe the jetting-out section in the ink-jetting device of the invention for producing a cell culture substrate. The piezoelectrically driving unit in the ink-jetting device of the invention for producing a cell culture substrate has a piezoelectrically driving unit for jetting out the cell-containing liquid supplied from the cell-containing liquid supplying section onto the cell culture patterning substrate through such as a hose, the temperature of which can be adjusted. This jetting-out section has a temperature controlling function.

In the invention, the width of openings in orifices of the piezoelectrically driving head is preferably set into the range of 20 to 500 μm. Preferably, the width is set into the range of about 20 to 250 μm in the case of using the cell-containing liquid of an ordinary type, and is set into the range of about 100 to 500 μm in the case of the above-mentioned microcapsules and the like. This makes it possible to supply the cell-containing liquid stably without damaging the cells in this liquid. The piezoelectrically driving head with orifices having such an opening width may be equivalent to an ordinary piezoelectrically driving head. Thus, detailed description thereof is omitted herein.

The temperature controlling means is not particularly limited if the means makes it possible to adjust the temperature of such as the channel extending from the cell-containing liquid supplying section and the temperature of the piezoelectrically driving head. Thus, the means may be the same as is ordinarily used as a temperature controlling temperature. Thus, description thereof is omitted herein.

3. Stage

The following will describe the stage. The stage which is used in the ink-jetting device of the invention is not particularly limited if the stage makes it possible to fix the cell culture patterning substrate, onto which the cell-containing liquid will be jetted out, and has a temperature controlling means for keeping the temperature thereof constant.

The temperature controlling means in the invention is not limited to any special type or structure if the means makes it possible to keep the substrate jetted out from the jetting-out section at a target temperature. Examples thereof include a means having a heating mechanism and a cooling mechanism for attaining cooling with, for example, water or a Peltier element.

4. Others

If necessary, the ink-jetting device of the invention for producing a cell culture substrate may appropriately have a member other than the above-mentioned members. It is particularly preferred that the device is provided with a humidity controlling means for controlling the humidity between the piezoelectrically driving head unit of the jetting-out section and the cell culture patterning substrate. This makes it possible to prevent cells from being dried to be annihilated between the piezoelectrically driving head unit and the cell culture patterning substrate.

The humidity controlling means may be a means for adjusting the humidity locally between the piezoelectrically driving head unit and the cell culture patterning substrate, or may be a means for adjusting the humidity of the whole of the ink-jetting device of the invention for producing a cell culture substrate.

It is preferred that the ink-jetting device of the invention is provided with a carbon dioxide concentration controlling means for adjusting the carbon dioxide concentration between the piezoelectrically driving head unit of the jetting-out section and the cell culture patterning substrate. The carbon dioxide concentration controlling means may be a means for adjusting the carbon dioxide concentration locally between the piezoelectrically driving head unit and the cell culture patterning substrate, or may be a means for adjusting the carbon dioxide concentration in the whole of the ink-jetting device of the invention for producing a cell culture substrate.

The present invention is not limited to the above-mentioned embodiments. The embodiments are mere examples, and all techniques having substantially the same technical concept and producing substantially the same advantageous effects as the techniques recited in the claims of the invention, and all equivalents thereof are included in the technical scope of the invention.

EXAMPLES

Hereinafter, examples are shown and thereby the present invention will be more specifically described.

Example 1

Patterning Substrate Forming Process (Formation of a Patterning Substrate)

The following were mixed: 5.0 g of an organosilane, TSL 8114 (manufactured by GE Toshiba Silicones), 0.55 g of a fluoroalkylsilane, TSL 8233 (manufactured by GE Toshiba Silicones), and 2.36 g of 0.005 N hydrochloric acid. The mixture was mixed 12 hours while stirred. This solution was diluted 100 times with isopropyl alcohol, and further the diluted solution was applied onto a soda glass substrate subjected beforehand to alkali treatment by spin coating. The substrate was dried at a temperature of 150° C. for 10 minutes, thereby forming a patterning substrate having a cell adhesion-inhibiting material layer, the properties of which were able to be changed from cell adhesion-inhibiting properties to cell adhesive properties by decomposition reaction based on a photocatalyst.

[Energy Irradiating Process]
(Formation of a Photomask Having a Photocatalyst-Containing Layer)

The following were mixed: 3 g of isopropyl alcohol, 0.4 g of an organosilane, TSL 8114 (manufactured by GE Toshiba Silicones), and 1.5 g of a photocatalyst inorganic coating agent, ST-K01 (manufactured by ISHIHARA SANGYO KAISHA, LTD). The mixture was then heated at 100° C. for 20 minutes while stirred.

This solution was diluted 10 times with isopropyl alcohol, and further the diluted solution was applied onto a quartz photomask substrate subjected beforehand to alkali treatment, on which a stripe pattern composed of light-shielding portions 500 μm in width and space portions 150 μm in width was formed, by spin coating. The substrate was dried at a temperature of 150° C. for 10 minutes to advance hydrolysis and polycondensation reaction, thereby forming a photomask having a photocatalyst-containing layer, 0.2 μm film thickness, wherein the photocatalyst was strongly fixed onto an organopolysiloxane.

(Energy Irradiation)

Ultraviolet rays were irradiated from a mercury lamp through the above-mentioned photomask onto the above-mentioned patterning substrate at an energy amount of 6 J/cm$^2$ to yield a cell culture patterning substrate having a cell adhesive surface patterned so as to have unexposed portions having cell adhesion-inhibiting properties and exposed portions having cell adhesive properties.

[Cell-Containing Liquid Applying Process]
(Preparation of a Cell-Containing Liquid)

The steps for preparing cell-containing liquids originating from various tissues are described in detail in, for example, "Soshikibaiyo no Gijyutsu, Dai San Han, Kiso", edited by The Japanese Tissue Culture Association and published by Asakura Shoten, and other documents. In the present process, primary human umbilical cord vein endothelial cells (HUVEC) were obtained by the method described on and after page 146 of this document.

(Application of the Cell-Containing Liquid)

An ink-jetting device (orifice width: 75 μm), a temperature and humidity adjusting device and a cell-containing liquid stirring device were fitted to an XY stage dispenser device manufactured by Sony Corporation, and then the cell-containing liquid was stirred therein at a temperature of 37° C.

The cell-containing liquid was inoculated onto the cell adhesion portions of the cell culture patterning substrate under the following environment conditions: a temperature of 37° C., a ratio by volume of 5% of carbon dioxide, a ratio by volume of 95% of air, and a relative humidity of 99%. The cell culture patterning substrate was then left as it was, so as to stand still for 2 hours. Next, this cell culture substrate was quietly arranged inside a culture dish, and a DMEM medium to which 10% fetal calf serum was added was attentively and quietly poured into the dish so as to culture the cells at 37° C. and a relative humidity of 90% in the environment of 5% by volume of carbon dioxide and 95% by volume of air for 16 hours.

The cells adhering onto the substrate was observed to recognize that the cells were oriented in the directions along all regions where the cells were cultured and the cells had an extended/developed shape.

The DMEM medium was exchanged with a DMEM medium to which 10 ng/ml of bFGF (manufactured by Sigma) was added. The culture of the cells was continued at 37° C. in the environment of 5% by volume carbon dioxide for 24 hours. It was observed that the cells formed a continuous capillary tissue.

Comparative Example

A plasma-treated culture dish was used instead of the cell culture patterning substrate to perform the same experiment as in Example 1. As a result, the cells adhered in a pattern form onto the dish but the cells were not oriented or extended/developed. Furthermore, even if the bFGF was added to the medium, a continuous capillary was not formed, and small tissue slices were formed at random.

Example 2

Patterning Substrate Forming Process, and Energy Irradiating Process

The same patterning substrate forming process and energy irradiating process as in Example 1 were performed except that an array-form photomask having openings, 1000 μm in size, arranged at intervals of 2000 μm was used, thereby forming a cell culture patterning substrate.

[Cell-Containing Liquid Applying Process]
(Preparation of Cell-Containing Microcapsules)

A cell-containing liquid was prepared in the same steps as in Example 1. Subsequently, a 40% solution of gelatin succinate (manufactured by Nippi Inc.) in pure water was stirred at 50° C. for 20 minutes. This gelatin solution and the previously-prepared cell-containing liquid were dropped down from coaxial nozzles having inside diameters of 300 μm and 200 μm, respectively, onto a Waymouth MB 752/1 medium solution, the temperature of which was heated to 25° C., thereby preparing microcapsules containing the cells.

(Application of the Cell-Containing Liquid)

In the same way as in Example 1, the cell-containing microcapsule solution was dropped down from an ink-jetting device, onto which a jetting-out head having orifices of 500 µm width was set, onto the cell adhesion portions of the cell culture patterning substrate, thereby patterning the cells. This substrate was allowed to stand still in an incubator 37° C. in temperature, to which $CO_2$ was added to give a ratio by volume of 5%, for 3 hours, thereby causing hepatocytes to adhere onto the substrate.

Next, the cell culture substrate onto which the cells adhered was immersed into a culture dish filled with a medium solution, and the culture of the cells was continued for 48 hours while the medium solution was exchanged. The cells were then observed with an optical microscope. As a result, it was recognized that the cells adhered in an array form along the cell adhesion portions on the cell culture patterning substrate.

Example 3

Patterning Substrate Forming Process

The following were mixed: 3 g of isopropyl alcohol, 0.4 g of an organosilane, TSL 8114 (manufactured by GE Toshiba Silicones), 0.04 g of N-(2-aminoethyl)-3-aminopropyltrimethoxysilane (manufactured by Huels America Inc.), and 1.5 g of a photocatalyst inorganic coating agent, ST-K01 (manufactured by ISHIHARA SANGYO KAISHA, LTD). The mixture was then heated at 100° C. for 20 minutes while stirred.

This solution was applied onto a quartz glass substrate subjected beforehand to alkali treatment by spin coating, and the substrate was dried at a temperature of 150° C. for 10 minutes to advance hydrolysis and polycondensation reaction, thereby forming a patterning substrate having a photocatalyst-containing cell adhesive layer, 0.2 µm in film thickness, containing the photocatalyst fixed strongly onto an organopolysiloxane and having properties changeable from cell adhesive properties to cell adhesion-inhibiting properties by action of the photocatalyst on the basis of energy irradiation.

[Energy Irradiating Process]

Ultraviolet rays were irradiated from a mercury lamp (wavelength: 365 nm) through a photomask onto this patterning substrate at an illuminance of 300 mW/cm² for 900 seconds to yield a cell culture patterning substrate wherein the resultant unexposed portions were cell adhesion portions and the resultant exposed portions were cell adhesion-inhibiting portions.

[Cell-Containing Liquid Applying Process]

A cell-containing liquid was applied onto the cell culture patterning substrate in the same way as in the cell-containing liquid applying process in Example 1. The cells adhering onto the substrate were then observed to recognize that the cells were oriented in the directions along all regions where the cells were cultured and the cell had an extended/developed shape.

The DMEM medium was exchanged with a DMEM medium to which 10 ng/ml of bFGF (manufactured by Sigma) was added. The culture of the cells was continued at 37° C. in the environment of 5% by volume carbon dioxide for 24 hours. It was observed that the cells formed a continuous capillary tissue.

Example 4

Patterning Substrate Forming Process

The following were mixed: 3 g of isopropyl alcohol, 0.4 g of an organosilane, TSL 8114 (manufactured by GE Toshiba Silicones), 0.04 g of a fluoroalkylsilane, TSL 8233 (manufactured by GE Toshiba Silicones), and 1.5 g of a photocatalyst inorganic coating agent, ST-K01 (manufactured by ISHIHARA SANGYO KAISHA, LTD). The mixture was then heated at 100° C. for 20 minutes while stirred.

This solution was applied onto a quartz substrate, on the rear face of which a light-shielding pattern composed of light-shielding portions of 300 µm width and opening portions of 60 µm width was formed, by spin coating. The substrate was dried at a temperature of 150° C. for 10 minutes to advance hydrolysis and polycondensation reaction, thereby forming a patterning substrate having a photocatalyst-containing cell adhesion-inhibiting material layer, 0.2 µm in film thickness, containing the photocatalyst fixed strongly onto an organopolysiloxane and having properties changeable from cell adhesion-inhibiting properties to cell adhesion properties by action of the photocatalyst on the basis of energy irradiation.

[Energy Irradiating Process]

Ultraviolet rays were irradiated from a mercury lamp (wavelength: 254 nm) onto the above-mentioned patterning substrate from the rear face side thereof at an exposure quantity of 5 J/cm² to yield a cell culture patterning substrate having a pattern wherein the resultant unexposed portions were cell adhesion-inhibiting portions and the resultant exposed portions were cell adhesion portions.

[Cell-Containing Liquid Applying Process]

A cell-containing liquid was applied onto the cell culture patterning substrate in the same way as in the cell-containing liquid applying process in Example 1. The cells adhering onto the substrate were then observed to recognize that the cells were oriented in the directions along all regions where the cells were cultured and the cell had an extended/developed shape.

The DMEM medium was exchanged with a DMEM medium to which 10 ng/ml of bFGF (manufactured by Sigma) was added. The culture of the cells was continued at 37° C. in the environment of 5% by volume carbon dioxide for 24 hours. It was observed that the cells formed a continuous capillary tissue.

Example 5

Patterning Substrate Forming Process (Formation of a Photocatalyst-Containing Layer)

The following were mixed: 3 g of isopropyl alcohol, 0.4 g of an organosilane, TSL 8114 (manufactured by GE Toshiba Silicones), and 1.5 g of a photocatalyst inorganic coating agent, ST-K01 (manufactured by ISHIHARA SANGYO KAISHA, LTD). The mixture was then heated at 100° C. for 20 minutes while stirred.

This solution was applied onto a quartz glass substrate subjected beforehand to alkali treatment by spin coating, and the substrate was dried at a temperature of 150° C. for 10 minutes to advance hydrolysis and polycondensation reaction, thereby forming, on the substrate, a photocatalyst-containing layer, 0.2 µm in film thickness, wherein the photocatalyst was fixed strongly onto an organopolysiloxane.

(Formation of a Cell Adhesive Layer)

There were mixed 0.2 mg of fibronection, F-4759 (manufactured by Sigma) and 200 ml of pure water, and this aqueous solution was dropped down onto the above-mentioned photocatalyst-containing layer, which was formed on the substrate, at a rate of 300 µl per cm² of the area of the substrate. This was allowed to stand still at 4° C. for 24 hours. Furthermore, the substrate was washed 2 times with PBS, and exposed to nitrogen gas so as to be dried, thereby yielding a patterning substrate having, on the substrate, the photocatalyst-containing layer and a cell adhesive layer.

[Energy Irradiating Process]

Subsequently, ultraviolet rays were irradiated from a mercury lamp, through a stripe-form photomask having light-shielding portions of 80 μm width and space portions of 300 μm width, onto this patterning substrate at 5 J/cm² (wavelength: 254 nm) to yield a cell culture patterning substrate having the cell adhesion layer patterned to have unexposed portions having cell adhesive properties and exposed portions having cell adhesion-inhibiting properties.

[Cell-Containing Liquid Applying Process]

A cell-containing liquid was applied onto the cell culture patterning substrate in the same way as in the cell-containing liquid applying process in Example 1. The cells adhering onto the substrate were then observed to recognize that the cells were oriented in the directions along all regions where the cells were cultured and the cell had an extended/developed shape.

The DMEM medium was exchanged with a DMEM medium to which 10 ng/ml of bFGF (manufactured by Sigma) was added. The culture of the cells was continued at 37° C. in the environment of 5% by volume carbon dioxide for 24 hours. It was observed that the cells formed a continuous capillary tissue.

Example 6

Patterning Substrate Forming Process (Formation of a Photocatalyst-Containing Layer)

The following were mixed: 3 g of isopropyl alcohol, 0.4 g of an organosilane, TSL 8114 (manufactured by GE Toshiba Silicones), and 1.5 g of a photocatalyst inorganic coating agent, ST-K01 (manufactured by ISHIHARA SANGYO KAISHA, LTD). The mixture was then heated at 100° C. for 20 minutes while stirred.

This solution was applied onto a quartz glass substrate subjected beforehand to alkali treatment by spin coating, and the substrate was dried at a temperature of 150° C. for 10 minutes to advance hydrolysis and polycondensation reaction, thereby forming, on the substrate, a photocatalyst-containing layer, 0.2 μm in film thickness, wherein the photocatalyst was fixed strongly onto an organopolysiloxane.

(Formation of a Cell Adhesion-Inhibiting Material Layer)

A solution composed of 5 g of isopropyl alcohol, 0.4 g of an organosilane, TSL 8114 (manufactured by GE Toshiba Silicones), and 0.04 g of a fluoroalkylsilane, TSL 8233 (manufactured by GE Toshiba Silicones) was applied onto this substrate by spin coating, and then the substrate was dried at 150° C. for 10 minutes, thereby forming a cell adhesion-inhibiting material layer.

[Energy Irradiating Process]

Ultraviolet rays were irradiated from a mercury lamp through a photomask onto this patterning substrate at 6 J/cm² (wavelength: 254 nm) to yield a cell culture patterning substrate having a cell adhesive surface patterned so as to have unexposed portions having cell adhesion-inhibiting properties and exposed portions having cell adhesive properties.

[Cell-Containing Liquid Applying Process]

A cell-containing liquid was applied onto the cell culture patterning substrate in the same way as in the cell-containing liquid applying process in Example 1. The cells adhering onto the substrate were then observed to recognize that the cells were oriented in the directions along all regions where the cells were cultured and the cell had an extended/developed shape.

The DMEM medium was exchanged with a DMEM medium to which 10 ng/ml of bFGF (manufactured by Sigma) was added. The culture of the cells was continued at 37° C. in the environment of 5% by volume carbon dioxide for 24 hours. It was observed that the cells formed a continuous capillary tissue.

Example 7

Patterning Substrate Forming Process

The following were mixed: 3 g of isopropyl alcohol, 0.4 g of an organosilane, TSL 8114 (manufactured by GE Toshiba Silicones), and 0.4 g of aminopropyltriethoxysilane. The mixture was then heated at 100° C. for 20 minutes while stirred. This solution was applied onto a quartz glass substrate subjected beforehand to alkali treatment by spin coating. The substrate was dried at a temperature of 150° C. for 10 minutes to advance hydrolysis and polycondensation reaction, thereby forming an organopolysiloxane layer, about 80 nm in film thickness, containing amino groups, on the substrate. In this way, a patterning substrate was formed.

[Energy Irradiating Process]

Energy irradiation was performed using a photomask having a photocatalyst-containing layer in the same way as in Example 1. This gave a cell culture patterning substrate having a cell adhesive surface patterned so as to have unexposed portions having cell adhesion properties and exposed portions having cell adhesion-inhibiting properties.

[Cell-Containing Liquid Applying Process]

A cell-containing liquid was applied onto the cell culture patterning substrate in the same way as in the cell-containing liquid applying process in Example 1. The cells adhering onto the substrate were then observed to recognize that the cells were oriented in the directions along all regions where the cells were cultured and the cell had an extended/developed shape.

The DMEM medium was exchanged with a DMEM medium to which 10 ng/ml of bFGF (manufactured by Sigma) was added. The culture of the cells was continued at 37° C. in the environment of 5% by volume carbon dioxide for 24 hours. It was observed that the cells formed a continuous capillary tissue.

Example 8

Patterning Substrate Forming Process, and Energy Irradiating Process

The following were mixed: 3 g of isopropyl alcohol, 0.2 g of an organosilane, TSL8114 (manufactured by GE Toshiba Silicones), and 0.2 g of PEG-silane (Methoxypolyethylene glycol 5,000 trimethylsilyl ether, Fluka). The mixture was heated at 100° C. for 20 minutes while stirred. This solution was applied onto a washed glass substrate (thickness: about 0.1 mm) by spin coating. Subsequently, the substrate was subjected to heating treatment at 150° C. for 10 minutes, thereby forming, on the substrate, a cell adhesion-inhibiting material layer, 160 nm in film thickness, made of an organopolysiloxane layer containing polyethylene glycol. In this way, a patterning substrate was yielded.

Next, the same energy irradiating process as in Example 1 was performed to form a cell culture patterning substrate. This cell culture patterning substrate was cut into a 21 mm square. Subsequently, a hole of 14 mm in diameter was made in the center of the bottom face of a commercially available plastic dish (manufactured by Corning Inc.) 35 mm in diameter. The glass substrate of the cut cell culture patterning substrate was stuck onto the plastic dish with an adhesive agent, KE45T (manufactured by Shin-Etsu Chemical Co. Ltd).

[Cell-Containing Liquid Applying Process]

The plastic dish was sterilized with a germicidal lamp, washed with PBS, and then washed with a DMEM medium. Thereafter, a cell-containing liquid was applied onto the dish and cells were cultured in the same way as in Example 1 except that no cell culture substrate was arranged in the dish. As a result, it was recognized that the cells were oriented along the cell adhesion portions inside the plastic dish and the cells had an extended/developed shape.

Example 9

A quartz substrate of about 0.1 mm thickness was used to form a cell culture patterning substrate and cut this cell culture patterning substrate into a 21 mm square in the same way as in Example 2. Thereafter, in the same way as in Example 8, the quartz substrate of the cut cell culture patterning substrate was stuck onto the same plastic dish as described above.

[Cell-Containing Liquid Applying Process]

A cell-containing liquid was applied into a plastic dish and cells were cultured in the same way as in Example 8. As a result, it was recognized that the cells were oriented along the cell adhesion portions inside the plastic dish and the cells had an extended/developed shape.

Example 10

A quartz substrate of about 0.1 mm thickness was used to form a cell culture patterning substrate and cut this cell culture patterning substrate into a 21 mm square in the same way as in Example 3. Thereafter, in the same way as in Example 8, the quartz substrate of the cut cell culture patterning substrate was stuck onto the same plastic dish as described above.

[Cell-Containing Liquid Applying Process]

A cell-containing liquid was applied into a plastic dish and cells were cultured in the same way as in Example 8. As a result, it was recognized that the cells were oriented along the cell adhesion portions inside the plastic dish and the cells had an extended/developed shape.

Example 11

A quartz substrate of about 0.1 mm thickness was used to form a cell culture patterning substrate and cut this cell culture patterning substrate into a 21 mm square in the same way as in Example 4. Thereafter, in the same way as in Example 8, the quartz substrate of the cut cell culture patterning substrate was stuck onto the same plastic dish as described above.

[Cell-Containing Liquid Applying Process]

A cell-containing liquid was applied into a plastic dish and cells were cultured in the same way as in Example 8. As a result, it was recognized that the cells were oriented along the cell adhesion portions inside the plastic dish and the cells had an extended/developed shape.

Example 12

A quartz substrate of about 0.1 mm thickness was used to form a cell culture patterning substrate and cut this cell culture patterning substrate into a 21 mm square in the same way as in Example 5. Thereafter, in the same way as in Example 8, the quartz substrate of the cut cell culture patterning substrate was stuck onto the same plastic dish as described above.

[Cell-Containing Liquid Applying Process]

A cell-containing liquid was applied into a plastic dish and cells were cultured in the same way as in Example 8. As a result, it was recognized that the cells were oriented along the cell adhesion portions inside the plastic dish and the cells had an extended/developed shape.

Example 13

A quartz substrate of about 0.1 mm thickness was used to form a cell culture patterning substrate and cut this cell culture patterning substrate into a 21 mm square in the same way as in Example 6. Thereafter, in the same way as in Example 8, the quartz substrate of the cut cell culture patterning substrate was stuck onto the same plastic dish as described above.

[Cell-Containing Liquid Applying Process]

A cell-containing liquid was applied into a plastic dish and cells were cultured in the same way as in Example 8. As a result, it was recognized that the cells were oriented along the cell adhesion portions inside the plastic dish and the cells had an extended/developed shape.

Example 14

A quartz substrate of about 0.1 mm thickness was used to form a cell culture patterning substrate and cut this cell culture patterning substrate into a 21 mm square in the same way as in Example 7. Thereafter, in the same way as in Example 8, the quartz substrate of the cut cell culture patterning substrate was stuck onto the same plastic dish as described above.

[Cell-Containing Liquid Applying Process]

A cell-containing liquid was applied into a plastic dish and cells were cultured in the same way as in Example 8. As a result, it was recognized that the cells were oriented along the cell adhesion portions inside the plastic dish and the cells had an extended/developed shape.

What is claimed is:

1. A method for producing a cell culture substrate, comprising:
    preparing a patterning substrate comprising a base material and a cell culture patterning layer formed on the base material and containing a cell adhesion-inhibiting material,
        wherein the cell adhesion-inhibiting material has cell adhesion-inhibiting properties which inhibits adhesion of cells and,
        wherein the cell adhesion-inhibiting material has cell adhesion properties resulting from the decomposing or denaturing action of a photocatalyst upon energy irradiation of the photocatalyst;
    preparing a photocatalyst-containing substrate comprising a base body and a photocatalyst-containing layer formed on the base body and containing a photocatalyst;
    arranging the cell culture patterning layer of the patterning substrate and the photocatalyst-containing layer of the photocatalyst-containing substrate to face each other so that the cell culture patterning layer and the photocatalyst-containing layer contact each other or face at a given interval;
    forming a pattern on the cell culture patterning layer composed of a cell adhesion-inhibiting portion wherein no photocatalyst action has been affected and a cell adhesion portion wherein the cell adhesion inhibiting material is decomposed or denatured by action of the photocatalyst, by irradiating with energy a region of the photocatalyst-containing layer facing a region of the cell culture patterning layer to which the cell adhesion portion is desired to be formed, and by affecting the action of the photocatalyst contained in the region of the photocatalyst-containing layer irradiated with energy to the facing cell culture patterning layer; and applying a cell-containing liquid onto the cell adhesion portion by a region-selecting applying method whereby the cell-containing liquid is selectively applied only onto the cell adhesion portion.

2. The method for producing a cell culture substrate according to claim 1, wherein the cell adhesion portion is a hydrophilic region and the cell adhesion-inhibiting portion is a water-repellent region.

3. The method for producing a cell culture substrate according to claim 1, wherein a plurality of light-shielding portions are formed on the base material or the photocatalyst-containing layer in the pattern form.

* * * * *